US011305022B2

(12) United States Patent
Bankiewicz et al.

(10) Patent No.: US 11,305,022 B2
(45) Date of Patent: Apr. 19, 2022

(54) METHODS FOR DISTRIBUTING HIGH LEVELS OF THERAPEUTIC AGENT THROUGHOUT THE CORTEX TO TREAT NEUROLOGICAL DISORDERS

(75) Inventors: Krystof Bankiewicz, Oakland, CA (US); Adrian P. Kells, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/146,640

(22) PCT Filed: Jan. 29, 2010

(86) PCT No.: PCT/US2010/022659
§ 371 (c)(1),
(2), (4) Date: Oct. 18, 2011

(87) PCT Pub. No.: WO2010/088560
PCT Pub. Date: Aug. 5, 2010

(65) Prior Publication Data
US 2012/0027726 A1 Feb. 2, 2012

Related U.S. Application Data
(60) Provisional application No. 61/148,302, filed on Jan. 29, 2009.

(51) Int. Cl.
| *A61K 48/00* | (2006.01) |
| *A61K 38/02* | (2006.01) |
| *A61P 25/00* | (2006.01) |
| *A61P 25/08* | (2006.01) |
| *A61P 25/18* | (2006.01) |
| *A61P 25/28* | (2006.01) |
| *C12N 15/86* | (2006.01) |

(52) U.S. Cl.
CPC .......... *A61K 48/0075* (2013.01); *C12N 15/86* (2013.01); *C12N 2750/14143* (2013.01)

(58) Field of Classification Search
CPC ............................ C12N 15/86; A61K 48/0075
See application file for complete search history.

(56) References Cited

U.S. PATENT DOCUMENTS

| 2005/0032219 | A1* | 2/2005 | Aubourg et al. | .............. 435/456 |
| 2006/0129126 | A1* | 6/2006 | Kaplitt | ............. A61M 25/00 604/513 |
| 2006/0171926 | A1 | 8/2006 | Passini et al. | |

FOREIGN PATENT DOCUMENTS

| WO | WO 03/004660 A1 | 1/2003 |
| WO | WO 03/018821 A2 | 3/2003 |
| WO | WO 2007/127839 A2 | 11/2007 |
| WO | WO-2007127839 A2 * | 11/2007 | .......... A61K 9/1271 |
| WO | WO 2009/059192 | * 5/2009 |

OTHER PUBLICATIONS

Kaplitt et al, (Lancet, 369: 2097-105, 2007).*
Bankiewicz (EP 1621625, published Jan. 2, 2006).*
Kaspar et al, Mol Ther, 2002, 50-56, 2002).*
Forsayeth et al (Molecular Therapy, 14(4): 571-577, 2006).*
Zerlip et al (J Neurosurg, 107: 560-567, 2007).*
Robertson (J Comp Neurol, 195(3): 501-25, 1981).*
Hadaczek et al (Human Gene Therapy, 17: 291-302, 2006).*
Bobo et al (PNAS, 91: 2076-2080, 1994).*
Hadaczek et al (Molecular Therapy, 14(1): 69-78, 2006.*
Gorelova et al (Neuroscience, 76(3): 689-706, 1996).*
Kells (PNAS, 106(7): 2407-2411, 2009). (Year: 2009).*
Rubio-Garrido (Neuroscience, 149: 242-250, 2007) (Year: 2007).*
Flanagan, 2008, "Traumatic brain injury: future assessment tools and treatment prospects", Neuropsychiatric Disease Treatment, 4(5): 877-92.*
Saavedra, et al. (2008) "Driving GDNF expression: the green and red traffic lights", Progress in Neurobiology, 86: 186-215.*
Bankiewicz, et al., "Long-term Clinical Improvement in MPTP-Lesioned Primates after Gene Therapy with AAV-hAADC," Mol Ther. 2006, 14: 564-570.
Barbon, et al., "AAV8-mediated hepatic expression of acid sphingomyelinase corrects the metabolic defect in the visceral organs of a mouse model of Niemann-Pick disease," Mol Ther, 2005, 12: 431-440.
Barranger, et al., "Gene therapy for lysosomal storage disorders," Expert Opin Biol Ther. 2001, 1: 857-867.
Bartlett, et al., "Selective and rapid uptake of adeno-associated virus type 2 in brain," Hum Gene Ther. 1998, 9: 1181-1186.
Bosch, et al., "Reversal of pathology in the entire brain of mucopolysaccharidosis type VII mice after lentivirus-mediated gene transfer," Hum Gene Ther. 2000, 11: 1139-1150.
Boulis, et al., "Adeno-associated viral vector gene expresion in the adult rat spinal cort following remote vector delivery," Neurobiol Dis. 2003, 14(3):535-541.
Brysch, et al., "The topology of the thalamo-cortical projections in the marmoset monkey (*Callithrix jacchus*)," Exp Brain Res. 1990, 81(1): 1-17.
Cearley, et al., "A single injection of an adeno-associated virus vector into nuclei with divergent connections results in widespread vector distribution in the brain and global correction of a neurogenetic disease," J Neurosci. 2007, 27(37): 9928-9940.
Christine, et al., "Safety and tolerability of putaminal AADC gene therapy for Parkinson's disease," Neurology In Press. 2009, 73(20): 1662-1669.
Crystal, et al., "Clinical protocol. Adminstration of a replication-deficient adeno-associated virus gene transfer vector expressing the human CLN2 cDNA to the brain of children with late infantile neuronal ceroid lipofuscinosis," Hum Gene Ther. 2004, 15: 1131-1154.

(Continued)

*Primary Examiner* — Robert M Kelly
(74) *Attorney, Agent, or Firm* — Todd Lorenz

(57) ABSTRACT

The invention provides methods for treating neurological disorders, which involve administering therapeutic agents to the thalamus by convection enhanced delivery.

13 Claims, 11 Drawing Sheets

(56) References Cited

OTHER PUBLICATIONS

Daadi, et al., "Distribution of AAV2-hAADC-transduced cells after 3 years in Parkinsonian monkeys," Neuroreport. 2006, 17: 201-204.
Dodge, et al., "Gene transfer of human acid sphingomyelinase corrects neuropathology and motor deficits in a mouse model of Niemann-Pick type A disease," Proc Natl Acad Sci US. 2005, 102: 17822-17827.
Eberling, et al., "Results from a phase I safety trial of hAADC gene therapy for Parkinson's disease," Neurology. 2008, 70: 1980-1983.
Fiandaca, et al., "Real-time MR imaging of adeno-associated viral vector delivery to the primate brain," Neuroimage, Academic Press, Orlando, FL. 2008, vol. 47 p. T27-T35.
Giguere M & Goldman-Rakic PS, "Mediodorsal nucleus: areal, laminar, and tangential distribution of afferents and efferents in the frontal lobe of rhesus monkeys," J Comp Neurol. 1988, 277(2): 195-213.
Goldman-Rakic PS & Porrino LJ, "The primate mediodorsal (MD) nucleus and its projection to the frontal lobe," J Comp Neurol. 1985, 242(4): 535-560.
Hsich, et al., "Critical issues in gene therapy for neurologic disease," Hum Gene Ther. 2002, 13: 579-604.
Jacobson, et al., "Corticothalamic neurons and thalamocortical terminal fields: an investigation in rat using horseradish peroxides and autoradiography," Brain Res, 1975, 85(3): 385-401.
Janson, et al., "Clinical protocol. Gene therapy of Canavan disease: AAV-2 vector for neurosurgical delivery of aspartoacylase gene (ASPA) to the human brain," Hum Gene Ther. 2002, 13: 1391-1412.
Kaspar, et al., "Retrograde viral delivery of IGF-1 prolongs survival in a mouse ALS model," Science, 2003, 301(5634): 839-842.
Kells, et al., "Efficient gene therapy-based method for the delivery of therapeutics to primate cortex," Proceedings of the National Academy of Sciences of the USA. 2009, 106: 2407-2411.
Kievit, et al., "Organization of the thalamo-cortical connexions to the frontal lobe in the rhesus monkey." Exp Brain Res. 1977, 29(3-4): 299-322.
Killackey, et al., "Corticothalamic projections from the rat primary somatosensory cortex." J Neurosci. 2003, 23(19): 7381-7384.
Kim, et al., "Expression and secretion of human glucocerebrosidase mediated by recombinant lentivirus vectors in vitro and in vivo: implications for gene therapy of Gaucher disease," Biochem Biophys Res Commun. 2004, 318: 381-390.
Marks, et al., "Safety and tolerability of intraputaminal delivery of CERE-120 (adeno-associated virus serotype 2-neurturin) to patients with idiopathic parkinson's disease: an open-label, phase I trial," Lancet Neurol. 2008, 7: 400-408.
Martin, et al., "Adeno-associated virus gene therapy of feline gangliosidosis," Molecular Genetics and Metabolism. 2009, 96(2): p. S30.
McFarland, et al., "Thalamic relay nuclei of the basal ganglia form both reciprocal and nonreciprocal cortical connections, linking multiple frontal cortical areas," J. Neurosci. 2002, 22: 8117-8132.
Passini, et al., "Combination brain and systemic injections of AAV provide maximal functional and survival benefits in the Niemann-Pick mouse," Proc Natl Acad Sci USA. 2007, 104: 9505-9510.
Passini, et al., "Identification of different modes of viral transport in the non-human primate brain after convection-enhanced deliery of AAV serotype vectors," Journal of Inherited Metabolic Disease. 2006, vol. 29, p. 30.
Passini, et al., "AAV vector-mediated correction of brain pathology in a mouse model of Niemann-Pick A disease," Mol Ther. 2005, 11: 754-762.
Peltola, et al., "Adenovirus-mediated gene transfer results in decreased lysosomal storage in brian and total correction in liver of aspartylglucosaminuria (AGU) mouse," Gene Ther. 1998, 5: 1314-1321.
San Sebastian, et al., "Adeno-associate virus type 6 is retrogradely transported in the non-human primate brain," Gene Therapey. Aug. 21, 2013: pp. 1-6.
Vite, et al., "Effective gene therapy for an inherited CNS disease in a large animal model," Ann Neurol. 2005, 57(3): 355-364.
Vite, et al., "Adeno-associated virus vector-mediated transduction in the cat brain," Gene Ther. 2003, 10(22): 1874-1881.
Watson, et al., "Lentiviral vectors for gene transfer to the central nervous system. Applications in lysosomal storage disease andimal models," Methods Mol Med. 2003, 76: 383-403.
Ziegler, et al., "Correction of enzymatic and lysosomal storage defects in Fabry mice by adenovirus-mediated gene transfer," Hum Gene Ther. 1999, 10: 1667-1682.

* cited by examiner

METHODS FOR DISTRIBUTING HIGH LEVELS OF THERAPEUTIC AGENT THROUGHOUT THE CORTEX TO TREAT NEUROLOGICAL DISORDERS

CROSS REFERENCE TO RELATED APPLICATIONS

This application claims priority to U.S. provisional patent application Ser. No. 61/148,302, filed Jan. 29, 2009, which is expressly incorporated herein in its entirety by reference.

STATEMENT REGARDING FEDERALLY SPONSORED RESEARCH OR DEVELOPMENT

This invention was made with Government support under Grant No. 5R01NS56107-2 awarded by the National Institutes of Health (NIH). The Government has certain rights in this invention.

FIELD

The invention relates to methods for treating neurological disorders involving the cortex, and methods of delivering therapeutic agents to the cortex.

BACKGROUND

The effective treatment of neurological disorders has been largely hindered by problems associated with the delivery of therapeutic agents to affected cell populations. Adequate delivery has been particularly problematic in neurological disorders involving the cortex.

For example, the use of gene therapy vectors to treat neurological disorders involving the cortex has remained a challenge due in large part to the physical constraints of effectively delivering a vector to a sufficient number of cortical neurons in affected areas. While multiple direct cortical infusions can be effective in small animal brains (e.g., Vite et al., Ann Neurol 57(3):355-364, 2005; and Vite et al., Gene Ther 10(22):1874-1881, 2003), as the architecture and volume of brain tissue increases in primates it becomes almost impossible to achieve widespread cortical delivery via direct cortical infusions. Although focal targeting of a specific nucleus can be reliably accomplished by stereotactic neurosurgical infusion, the extensive convoluted arrangement of the primate cerebral cortex is not easily targeted by direct infusion of viral vectors.

Axonal and transynaptic transport of viral vectors, and expression of vector-encoded genes at sites distal to sites of injection have been reported. For example, Aubourg et al., US 2005/0032219, discloses that injection of a recombinant adeno-associated virus (AAV) into the corpus callosum and pons resulted in gene expression at a number of sites connected to the injection site, including the anterior cerebral cortex, olfactory bulb, striatum, thalamus, optic nuclei, inferior colliculus and spinal cord. Additionally, Passini et al., US 2006/0171926, discloses that injection of a recombinant AAV into the hippocampus in a mouse model of lysosomal storage disease resulted in gene expression in the contralateral dentate gyrus, CA3 region, medial septum, and entorhinal cortex. In each of the reported rodent models, however, there was only limited expression in certain areas of the cortex, and the correlation of the designated transport pathways to corresponding pathways in the primate brain remains unclear.

Consequently, the difficulties in safely achieving widespread therapeutic distribution in the human brain have hindered the development of potential treatments for a variety of neurological disorders impacting large cortical domains, including traumatic brain injury, stroke, enzymatic dysfunction disorders, and dementias.

SUMMARY OF THE INVENTION

The present inventors have found that unprecedented volumes of distribution of therapeutic agent within the primate cortex can be achieved by convection enhanced delivery (CED) of therapeutic agents to the thalamus. Using the methods disclosed herein, high levels and widespread cortical distribution of therapeutic agent can be achieved with even a single administration to the primate thalamus. As a result, neurological disorders such as traumatic brain injury, stroke, enzymatic dysfunction disorders, dementias and other neurological disorders impacting large areas of cortex are therapeutically accessible via CED to the thalamus. Delivery to the thalamus by CED obviates the need for direct and repeated delivery to multiple sites in the cortex, which has impeded the treatment of many neurological disorders. Further, the present methods employ anterograde transport, which remains functional while cortical neurons and the retrograde transport facilitated thereby may be compromised in many neurological disorders. Additionally, therapeutic agents can be further delivered to tertiary sites connected to the cortical domains supplied with therapeutic agent by thalamic delivery, increasing the scope of cell populations and disorders that may be treated by the current methods.

Although the present invention concerns axonal transport, the invention stems from the previously unobserved, extraordinary capacity of primate thalamocortical projections to convey therapeutic agents to the cortex when delivered by adequate means to the thalamus. Notwithstanding demonstrations of transport phenomena in small laboratory animals and non-thalamocortical pathways (e.g., US 2006/0171926, US 2005/0032219), the presently disclosed capacity of primate thalamocortical projections to anterogradely deliver large amounts of viral vector to widespread regions of the primate cortex and achieve therapeutically relevant volumes of distribution in large cortical domains remained unknown. Further, as detailed herein, CED of therapeutic vector to the thalamus appears to be necessary to achieve thalamic levels that facilitate high level expression and widespread distribution in the cortex and obviate the need for direct cortical delivery to affected cortical areas to treat particular neurological disorders.

Accordingly, in one aspect, the invention provides methods for treating neurological disorders involving the cortex, referred to herein as "cortical neurological disorders". The methods involve delivery of therapeutic agents to the thalamus by CED.

Preferred cortical neurological disorders are those that involve large areas of the cortex, preferably more than one functional area of the cortex, preferably more than one lobe of the cortex, and up to and including the entire cortex. Preferred cortical neurological disorders include, but are not limited to, traumatic brain injury; stroke; enzymatic dysfunction disorders; psychiatric disorders, including post-traumatic stress syndrome; neurodegenerative diseases, including Huntington's disease, Parkinson's disease and Alzheimer's disease; epilepsy; and cognitive disorders, including dementias, autism, and depression. Preferred enzymatic dysfunction disorders include, but are not limited to leukodystrophies, including Canavan's disease, and lysosomal storage diseases (LSD), including Niemann-Pick disease, Gaucher disease, Batten disease, Fabry disease and Pompe disease.

In a preferred embodiment, the cortical neurological disorder involves at least a first and a second population of cortical neurons that are innervated by thalamocortical projections originating in a first and second thalamic nucleus, respectively, wherein the thalamic nuclei are different.

In a preferred embodiment, the cortical neurological disorder involves more than one functional area of the cortex.

In a preferred embodiment, the cortical neurological disorder involves more than one lobe of the cortex.

In one embodiment, the cortical neurological disorder involves a tertiary neuronal population connected to the cortex.

In a preferred embodiment, the therapeutic agent delivered to the thalamus is a viral particle comprising a therapeutic nucleic acid. In a preferred embodiment, the viral particle is an AAV particle. In a preferred embodiment, the AAV particle is selected from the group consisting of AAV2, AAV3, AAV4, AAV5, AAV6, AAV7, AAV8, and AAV9.

In a preferred embodiment, the viral particle comprises a nucleic acid encoding a therapeutic protein. In one embodiment, the therapeutic protein is an enzyme. In one embodiment, the therapeutic protein is selected from the group consisting of growth factors, including neurotrophins; hormones; immunomodulatory peptides and proteins, including cytokines; and neuromodulatory peptides.

In one embodiment, the cortical neurological disorder is Niemann-Pick disease type-A, and the therapeutic protein is human acid sphingomyelinase.

In a preferred embodiment, the encoded therapeutic protein is produced in the brain for at least six months after delivery.

In one embodiment, the therapeutic agent delivered to the thalamus is a therapeutic protein. The subject therapeutic proteins are capable of translocation to the cortex. In one embodiment, the therapeutic protein is an enzyme. In one embodiment, the therapeutic protein is selected from the group consisting of growth factors, including neurotrophins; hormones; immunomodulatory peptides and proteins, including cytokines; and neuromodulatory peptides.

In one embodiment, the cortical neurological disorder is Niemann-Pick disease type-A, and the therapeutic protein is human acid sphingomyelinase.

In one embodiment, the method comprises a single infusion of therapeutic agent to the thalamus by CED. In another embodiment, the method comprises more than one infusion of therapeutic agent to the thalamus by CED.

In a preferred embodiment, the therapeutic agent is delivered to more than one location in the thalamus. In one embodiment, the therapeutic agent is delivered to more than one location using more than one cannula.

In a preferred embodiment, the therapeutic agent is delivered bilaterally to the thalamus.

In a preferred embodiment, the therapeutic agent is delivered bilaterally to corresponding thalamic nuclei.

In one embodiment, the method further comprises delivering the therapeutic agent to the brainstem.

In one embodiment, delivery by CED comprises stepping.

In a preferred embodiment, a tracing agent, preferably an MRI contrast enhancing agent, is co-delivered with the therapeutic agent infusate to provide for real-time monitoring of tissue distribution of infusate.

In one aspect, the invention provides methods for delivering a therapeutic agent to the cortex in a primate, comprising delivering a therapeutic agent to the thalamus by CED.

In a preferred embodiment, the therapeutic agent is delivered to more than one location in the thalamus. In one embodiment, the therapeutic agent is delivered to more than one location using more than one catheter.

In a preferred embodiment, the therapeutic agent is delivered to at least a first and a second population of cortical neurons that are innervated by thalamocortical projections originating in a first and second thalamic nucleus, respectively, wherein the thalamic nuclei are different.

In a preferred embodiment, the therapeutic agent is delivered to more than one functional area of the cortex.

In a preferred embodiment, the therapeutic agent is delivered to more than one lobe of the cortex.

In a preferred embodiment, the therapeutic agent is a viral particle comprising a nucleic acid encoding a therapeutic protein.

In a preferred embodiment, the viral particle is an AAV particle. In a preferred embodiment, the AAV particle is selected from the group consisting of AAV2, AAV3, AAV4, AAV5, AAV6, AAV7, AAV8, and AAV9.

In one embodiment, the therapeutic agent is a protein.

In a preferred embodiment, the therapeutic agent is delivered to more than one location in the thalamus. In one embodiment, the therapeutic agent is delivered to more than one location using more than one cannula.

In a preferred embodiment, the therapeutic agent is delivered bilaterally to the thalamus.

In a preferred embodiment, the therapeutic agent is delivered bilaterally to corresponding thalamic nuclei.

In one embodiment, the method further comprises delivering the therapeutic agent to the brainstem.

In one embodiment, delivery by CED comprises stepping.

In a preferred embodiment, a tracing agent, preferably an MRI contrast enhancing agent, is co-delivered with the therapeutic agent infusate to provide for real-time monitoring of tissue distribution of infusate.

DETAILED DESCRIPTION

Figure 1:
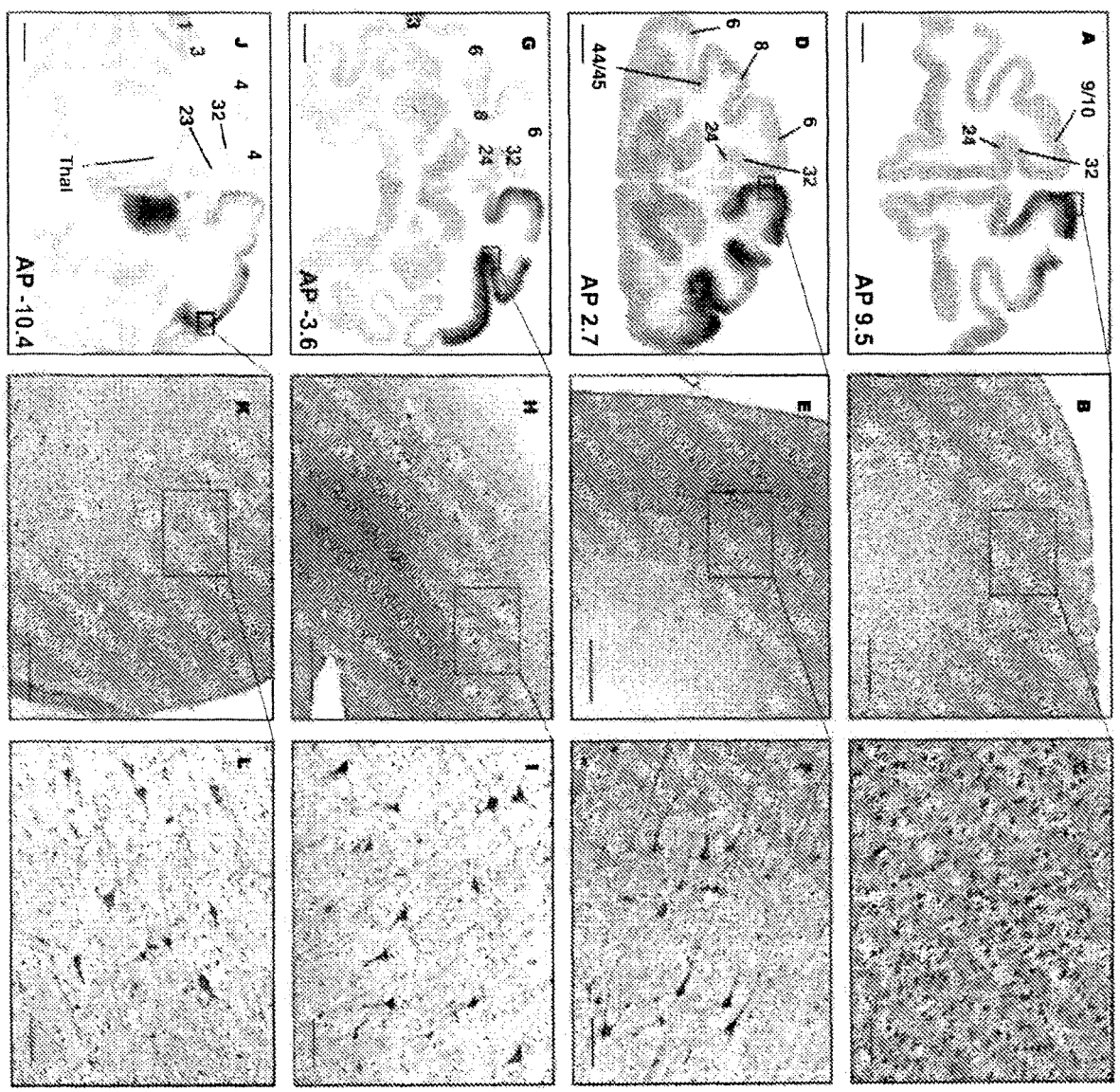
FIG. 1. Distribution of GDNF protein after AAV2-GDNF infusion into the thalamus. (A) GDNF expression detected by IHC staining in the pre-frontal cortex ipsilateral to thalamic infusion. (B, C) Large numbers of non-pyramidal GDNF-positive neurons were found across multiple layers in cortical Area 8. (D, G) GDNF IHC staining in the cingulate cortex, pre-motor cortex, and lateral pre-frontal cortex. (E, F, H, I) Pyramidal neurons in lamina V and VI of the pre-motor cortex (Area 6) expressing GDNF. Strong GDNF-immunopositive staining is evident in the cortical layers above the pyramidal neurons. (J) Intensive GDNF-positive staining in the infused thalamus and cortical GDNF expression in the somatosensory cortex (Area 3) and motor cortex (Area 4). (K,L) GDNF-positive neurons in lamina V and VI of the somatosensory cortex. AP: Anterior/Posterior distance in mm from bregma. Scale bars: 500 µm (B, E, H, K), 100 µm (C, F, I, L).

"Cortical neurological disorder", as used herein, refers to a neurological disorder involving the cortex. Cortical neurological disorders are neurological disorders that (i) involve a population of cells in the cortex that is directly anatomically connected to the thalamus, and/or (ii) involve a population of cells that is directly anatomically connected to the cortical cell population in (i). Preferred cortical neurological disorders are those that involve large areas of the cortex, preferably more than one functional area of the cortex, preferably more than one lobe of the cortex, and up to and including the entire cortex. Preferred cortical neurological disorders include, but are not limited to, traumatic brain injury; stroke; enzymatic dysfunction disorders; psychiatric disorders, including post-traumatic stress syndrome; neurodegenerative diseases, including Huntington's disease, Parkinson's disease and Alzheimer's disease; epilepsy; and cognitive disorders, including dementias, autism, and depression. Preferred enzymatic dysfunction disorders include, but are not limited to leukodystrophies, including Canavan's disease, and lysosomal storage diseases (LSD), including Niemann-Pick disease, Gaucher disease, Batten disease, Fabry disease and Pompe disease. This list of disorders is exemplary and non-limiting. It will be apparent to the reasonably skilled artisan which neurological disorders are suitable for treatment by the present methods based on cortical pathology and neuroanatomical connectivity.

"Cortex" as used herein refers to the cerebral cortex.

Method of Administration

The present methods involve direct delivery of therapeutic agents to the thalamus. Delivery is done by convection enhanced delivery (CED) to achieve effective transport of therapeutic agent in patients. The terms "patient", "subject", and "individual" are used interchangeably herein and refer to large mammals, preferably primates, and most preferably humans. "Patient" does not include small mammals such as rodents.

By "CED" is meant infusion at a rate greater than 0.5 μL/min. CED is preferably done using a suitable catheter or cannula, preferably a step-design reflux-free cannula. The method involves positioning the tip of the cannula at least in close proximity to the target thalamic tissue, and preferably the tip is inserted into the thalamus. After the cannula is positioned, it is connected to a pump which delivers the therapeutic agent through the cannula tip to the target thalamic tissue. A pressure gradient from the tip of the cannula is maintained during infusion. Intraoperative MRI (iMRI) and use of tracing agent to monitor infusion are highly preferred.

By "proximal to" a target thalamic population is meant within an effective distance of the target population. In particular, with respect to the positioning of a cannula relative to target thalamic tissue, proximity refers to a distance such that infusate will reach the target tissue when delivered by CED.

In a preferred embodiment, CED comprises an infusion rate of between 0.5 μL/min and 10 μ/min.

In a preferred embodiment, CED comprises an infusion rate of greater than about 0.5 µL/min, more preferably greater than about 0.7 µL/min, more preferably greater than about 1 µL/min, more preferably greater than about 1.2 µL/min, more preferably greater than about 1.5 µL/min, more preferably greater than about 1.7 µL/min, more preferably greater than about 2 µL/min, more preferably greater than about 2.2 µL/min, more preferably greater than about 2.5 µL/min, more preferably greater than about 2.7 µL/min, and more preferably greater than about 3 µL/min, as well as preferably less than about 25 µL/min, more preferably less than 20 µL/min, more preferably less than about 15 µl/min, more preferably less than about 12 µl/min, and more preferably less than about 10 µL/min.

In a preferred embodiment, CEO comprises incremental increases in flow rate, referred to as "stepping", during delivery. Preferably, stepping comprises infusion rates of between 0.5 µL/min and 10 µL/min.

In a preferred embodiment, stepping comprises infusion rates of greater than about 0.5 µL/min, more preferably greater than about 0.7 µL/min, more preferably greater than about 1 µL/min, more preferably greater than about 1.2 µL/min, more preferably greater than about 1.5 µL/min, more preferably greater than about 1.7 µL/min, more preferably greater than about 2 µL/min, more preferably greater than about 2.2 µL/min, more preferably greater than about 2.5 µL/min, more preferably greater than about 2.7 µL/min, and more preferably greater than about 3 µL/min, as well as preferably less than about 25 µL/min, more preferably less than 20 µL/min, more preferably less than about 15 µL/min, more preferably less than about 12 NL/min, and more preferably less than about 10 µL/min.

In a preferred embodiment, a step-design reflux-free cannula is joined with a pump that produces enough pressure to cause the infusate to flow through the cannula to the target tissue at controlled rates. Any suitable flow rate can be used such that the intracranial pressure is maintained at suitable levels so as not to injure the brain tissue. More than one cannula can be used, but a single cannula is preferred.

Delivery may be done once or more than once, as is appropriate for the cortical neurological disorder being treated and the patient response, and which is readily determinable by the reasonably skilled artisan.

In one embodiment, penetration is further augmented by the use of a facilitating agent. A facilitating agent is capable of further facilitating the delivery of infusate to target tissue. A facilitating agent is particularly preferred when the therapeutic agent delivered is a therapeutic protein. Particularly preferred is low molecular weight heparin. See, for example, U.S. Ser. No. 11/740,124, filed 25 Apr. 2007, which is expressly incorporated herein by reference.

In a highly preferred embodiment, a tracing agent, preferably an MRI contrast enhancing agent, is co-delivered with the therapeutic agent infusate to provide for real-time monitoring of tissue distribution of infusate. See for example Fiandaca et al., NeuroImage, 2008 Nov. 27 (Epub ahead of print). See for example U.S. Ser. No. 11/740,508, filed 26 Apr. 2007, as well as U.S. Ser. No. 11/740,124, filed 25 Apr. 2007, which are expressly incorporated herein by reference. Use of a tracing agent may inform the cessation of delivery. Other tracing and imaging means known in the art may also be used to follow infusate distribution.

Any suitable amount of infusate can be administered in this manner. Suitable amounts are amounts that are therapeutically effective without causing an overabundance of undesirable side effects. For viral particle infusates, suitable amounts will depend on titre, infectivity, the volume of the target tissue, nature of the active agent, and additional factors, as recognized by one of skill in the art. The $V_i:V_d$ ratio is preferably at least 1:1.

For further teaching on the method of CED, see for example Saito et al., Exp. Neural., 196:381-389, 2005; Krauze et al., Exp. Neural., 196:104-111, 2005; Krauze et al., Brain Res. Brain Res. Protocol., 16:20-26, 2005; U.S. Patent Application Publication No. 2006/0073101; and U.S. Pat. No. 5,720,720, each of which is incorporated herein by reference in its entirety. See also Noble et al., Cancer Res. Mar. 1, 2006; 66(5):2801-6; Saito et al., J Neurosci Methods. Jun. 30, 2006; 154(1-4225-32; Hadaczek et al., Hum Gene Ther. March 2006; 17(3):291-302; and Hadaczek et al., Mol. Ther. July 2006; 14(1):69-78, each of which is incorporated herein by reference in its entirety.

See also U.S. Ser. No. 11/740,548 filed Apr. 26, 2007, which is expressly incorporated herein in its entirety by reference. See also U.S. Pat. No. 6,953,575, which is expressly incorporated herein in its entirety by reference.

In a highly preferred embodiment, the method of CED is done with a CED-compatible reflux-free step design cannula. Such highly preferred cannulas are disclosed in Krauze et al., J. Neurosurg. November 2005; 103(5):923-9, incorporated herein by reference in its entirety, and in U.S. Patent Application Publication No. US 2006/0135945 A1, incorporated herein by reference in its entirety, and U.S. Patent Application Publication No. US 2007/0088295 A1, incorporated herein by reference in its entirety. Further regarding preferred cannulas for use in the subject invention, see PCT/US08/64011.

Exemplary pump systems for use in the subject invention include the implantable systems described in U.S. Pat. Nos. 7,351,239; 7,341,577; 6,042,579; 5,735,815 and 4,692,147.

The present methods of treatment optionally involve one or more pre-operative diagnostic determinations of the presence of a cortical neurological disorder. The diagnostic determination done preferably includes neuroimaging. In one embodiment, the diagnostic determination involves a genetic test. The methods also preferably involve pre-operative imaging to stereotactically define the location of the targeted thalamic population.

In a preferred embodiment, the methods additionally comprise imaging during administration in order to monitor cannula positioning. In one embodiment, the method comprises use of a neuronavigation system, for example, see U.S. Patent Application Publication No. 2002/0095081, incorporated herein by reference in its entirety.

In one aspect, the invention provides methods of compiling data obtained from image-based monitoring of infusate distribution as delivered by CED. The data may include but is not limited to volume of infusate, volume of distribution, neuroanatomical distribution, genetic data, infusion parameters, cannula parameters, and cannula placement data. In one embodiment the invention provides a database comprising such data. In one embodiment, the database is useful for deriving algorithms describing the distribution of infusate in the CNS of a patient having a cortical neurological disorder and may be used to model therapeutic delivery.

It is contemplated that combinations of the subject therapeutic agents may be used in methods herein. For example, it is contemplated that more than one type of viral particle may be used, and that a viral particle infusate may be administered with an effective amount of a second therapeutic agent in a combination therapy. The second agent may or may not be delivered to the thalamus.

The particular thalamic nuclei to which therapeutic agents are delivered will depend on the cortical neurological disorder being treated. It will be apparent to the reasonably skilled artisan which cortical populations are affected in any given cortical neurological disorder, and consequently, which thalamic nuclei should be targeted, based on neuroanatomical knowledge in the art. For example, see McFarland et al., J. Neurosci., 22:8117-8132, 2002, which is expressly incorporated herein by reference. In a preferred embodiment, therapeutic agent is delivered to a plurality of thalamic nuclei. Such delivery may be done with one or more infusion cannulae. For disorders involving relatively more discrete cortical regions, and/or tertiary CNS populations innervating such relatively more discrete cortical domains, and especially where the therapeutic agent may have undesirable effects in a cortical region outside the target cortical domains, therapeutic agent is delivered to one or more select thalamic nuclei innervating the target cortical domains thereby restricting cortical distribution to the desired cortical domains.

In one embodiment, the methods comprise administration of the therapeutic to a single thalamic location. In another embodiment, the methods comprise administration of the therapeutic to more than one thalamic location. In one embodiment, the methods comprise administering the therapeutic agent bilaterally. In a preferred embodiment, the methods comprise administration of the therapeutic bilaterally to corresponding thalamic nuclei.

Any thalamic nucleus that projects to an affected region of cortex may be targeted for delivery where appropriate for the cortical neurological disorder being treated. In a preferred embodiment, the methods comprise delivery of therapeutic agent to one or more thalamic nuclei selected from the group consisting of anterior nuclear group, medial dorsal nucleus, ventral, ventral anterior, ventral lateral, ventral posterolateral, ventral posteromedial, lateral nuclear group, midline nuclear group, pulvinar, lateral or medial geniculate nucleus.

In one embodiment, the methods further comprise administration of the therapeutic to the brainstem. This embodiment is especially preferred where the neurological disorder of the cortex further involves the brainstem. For example, an additional administration of therapeutic to the brainstem is desirable for the treatment of the respiratory aspect of many cortical neurological disorders, including lysosomal storage diseases.

Therapeutic Proteins for Thalamic Delivery

The therapeutic proteins that may be delivered to the thalamus are capable of translocation to the cortex. In one embodiment, the therapeutic protein is an enzyme. In one embodiment, the therapeutic protein is selected from the group consisting of growth factors, including neurotrophins; hormones; immunomodulatory peptides and proteins, including cytokines; and neuromodulatory peptides.

In a preferred embodiment, a therapeutic protein of the invention is selected from the group consisting of NGF, BDNF, NT-3, NT-4/5, NT-6, GDNF, CNTF, LIF, IGF-1, b-FGF, neurturin, persephin, artemin, TGFα, TGFβ, IGF-2, PDGF, EGF, cardiotropin, EGF, IGF, VEGF, Sonic hedgehog (SHH), BMP, FGF20, VIP, PDGF, pleiotrophin (PTN), and HGF.

Included among therapeutic proteins are therapeutic protein derivatives, including growth factor derivatives.

For further discussion of therapeutic proteins, see for example U.S. Ser. No. 11/740,124, filed 25 Apr. 2007, which is expressly incorporated herein in its entirety by reference. Therapeutic proteins that may be delivered to the thalamus include proteins encoded by therapeutic nucleic acids as described below, wherein the therapeutic protein is capable of translocation to the cortex.

Viral Particles and Gene Transfer

In one embodiment, the present methods comprise transduction of a thalamic neuron by a viral particle comprising a nucleic acid encoding a therapeutic protein, expression of the therapeutic protein in the thalamic neuron, and anterograde transport of the therapeutic protein to the cortex.

In one embodiment, the present methods comprise anterograde translocation of a viral particle comprising a nucleic acid encoding a therapeutic protein to a neuron in the cortex, transduction of the cortical neuron, and expression of the therapeutic protein in the cortical neuron.

In one embodiment, the present methods comprise transduction of a thalamic neuron by a first viral particle comprising a nucleic acid encoding a therapeutic protein, expression of the therapeutic protein in the thalamic neuron, and anterograde transport of the therapeutic protein to the cortex, as well as anterograde translocation of a second viral particle comprising a nucleic acid encoding a therapeutic protein to a neuron in the cortex, transduction of the cortical neuron, and expression of the therapeutic protein in the cortical neuron.

In one embodiment, the methods further comprise translocation of the viral particle and/or the therapeutic protein to a tertiary neuronal population connected to the region of cortex in which the cortical neuron receiving therapeutic agent from the thalamus is located. The tertiary site may be a location in the telencephalon that is not directly connected to the subject thalamic nuclei. In an especially preferred embodiment, the tertiary site is the basal forebrain. Such methods are highly preferred for the treatment of Alzheimer's disease.

Any viral particle that can carry a therapeutic nucleic acid and transduce a thalamic and/or cortical neuron such that a therapeutic agent (e.g., an encoded therapeutic protein) is produced can be used in the invention. Where the virus is able to produce therapeutic agent in a cortical neuron but not in a thalamic neuron, the virus must be capable of translocation. Where the virus is able to produce therapeutic agent in a thalamic neuron but not in a cortical neuron, the therapeutic agent must be capable of translocation to the cortex.

A preferred viral particle for use in the invention is one that is capable of translocation from the thalamus to the cortex.

Included among preferred viral particles are adeno-associated viruses (AAV). AAVs 1-11 are included, as hybrids (e.g., see Choi et al., "AAV Hybrid Serotypes: Improved Vectors for Gene Delivery", Curr Gene Ther. 2005 June; 5(3): 299-310). Preferred AAVs include but are not limited to AAV2, AAV3, AAV4, AAV5, AAV6, AAV7, AAV8, and AAV9. Particularly preferred is AAV2. As used herein, "AAV" refers to recombinant AAVs (i.e., those engineered to carry therapeutic nucleic acids), as well as native AAVs. Recombinant AAVs are also referred to herein as "rAAVs".

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells. A number of systems have been developed for gene transfer into mammalian cells. See, e.g., U.S. Pat. No. 5,399,346, which is expressly incorporated herein in its entirety by reference.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By "recombinant virus" is meant a virus that has been genetically altered, e.g., by the addition or insertion of a heterologous nucleic acid construct into the particle.

By "AAV virion" or "AAV particle" is meant a complete virus particle, such as a wild-type (wt) AAV virus particle (comprising a linear, single-stranded AAV nucleic acid genome associated with an AAV capsid protein coat), or a recombinant AAV particle. In this regard, single-stranded AAV nucleic acid molecules of either complementary sense, e.g., "sense" or "antisense" strands, can be packaged into any one AAV virion and both strands are equally infectious.

A "recombinant AAV virion," sometimes referred to as an "rAAV virion" or "rAAV particle" is preferably an infectious, replication-defective virus composed of an AAV protein shell, encapsidating a heterologous nucleotide sequence of interest which is flanked on both sides by AAV ITRs. A rAAV virion may be produced in a suitable host cell which has had an AAV vector, AAV helper functions and accessory functions introduced therein. In this manner, the host cell is rendered capable of encoding AAV polypeptides that are required for packaging the AAV vector (containing a recombinant nucleotide sequence of interest) into infectious recombinant virion particles for subsequent gene delivery.

The term "transfection" or "transduction" is used to refer to the uptake of foreign DNA by a cell, and a cell has been "transfected" or "transduced" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties, such as a nucleotide integration vector and other nucleic acid molecules, into suitable host cells.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The term captures sequences that include any of the known base analogues of DNA and RNA such as, but not limited to 4-acetylcytosine, 8-hydroxy-N-6-methyladenosine, aziridinylcytosine, pseudoisocytosine, 5-(carboxyhydroxylmethyl)uracil, 5-fluorouracil, 5-bromouracil, 5carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term DNA "control sequences" includes but is not limited to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

A "gene" refers to a polynucleotide containing at least one open reading frame that is capable of encoding a particular polypeptide or protein after being transcribed or translated. Any of the polynucleotide sequences described herein may be used to identify larger fragments or full-length coding sequences of the genes with which they are associated. Methods of isolating larger fragment sequences are know to those of skill in the art.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., Molecular Cloning: A Laboratory Manual, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, Nucleic Acid Hybridization: A Practical Approach, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., Molecular Cloning: A Laboratory Manual, Second Edition, (1989) Cold Spring Harbor, N.Y.).

Techniques for determining nucleic acid and amino acid "sequence identity" or "homology" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+Gen Bank CDS translations+Swiss protein+Spupdate+PIR. Details of these programs can be found at the following internet address: www.ncbi.nlm.govicgi-bin/BLAST.

Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 90%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

Construction of Viral Vectors

Gene delivery vehicles useful in the practice of the present invention can be constructed utilizing methodologies well known in the art of molecular biology (see, for example, Ausubel or Maniatis, supra). The descriptions herein are to be construed as exemplary, and not limiting. Typically, viral vectors carrying transgenes are assembled from polynucleotides encoding or corresponding to the transgene(s), suitable regulatory elements and elements necessary for production of viral proteins which mediate cell transduction. For example, in a preferred embodiment, adeno-associated viral (AAV) vectors are employed.

General Methods

A preferred method of obtaining the nucleotide components of the viral vector is PCR. General procedures for PCR are taught in MacPherson et al., PCR: A PRACTICAL APPROACH, (IRL Press at Oxford University Press, (1991)). PCR conditions for each application reaction may be empirically determined. A number of parameters influence the success of a reaction. Among these parameters are annealing temperature and time, extension time, $Mg^{2+}$ and ATP concentration, pH, and the relative concentration of primers, templates and deoxyribonucleotides. After amplification, the resulting fragments can be detected by agarose gel electrophoresis followed by visualization with ethidium bromide staining and ultraviolet illumination.

Another method for obtaining polynucleotides is by enzymatic digestion. For example, nucleotide sequences can be generated by digestion of appropriate vectors with suitable recognition restriction enzymes. The resulting fragments can then be ligated together as appropriate.

Polynucleotides are inserted into vector genomes using methods well known in the art. For example, insert and vector DNA can be contacted, under suitable conditions, with a restriction enzyme to create complementary or blunt ends on each molecule that can pair with each other and be joined with a ligase. Alternatively, synthetic nucleic acid linkers can be ligated to the termini of a polynucleotide. These synthetic linkers can contain nucleic acid sequences that correspond to a particular restriction site in the vector DNA. Other means are known and available in the art.

Retro viral and Adenoviral Vectors

A number of viral based systems have been used for gene delivery. See for example U.S. Pat. No. 5,576,201, which is expressly incorporated herein by reference. For example, retroviral systems are known and generally employ packaging lines which have an integrated defective provirus (the "helper") that expresses all of the genes of the virus but cannot package its own genome due to a deletion of the packaging signal, known as the psi sequence. Thus, the cell line produces empty viral shells. Producer lines can be derived from the packaging lines which, in addition to the helper, contain a viral vector which includes sequences required in cis for replication and packaging of the virus, known as the long terminal repeats (LTRs). The gene of interest can be inserted in the vector and packaged in the viral shells synthesized by the retroviral helper. The recombinant virus can then be isolated and delivered to a subject. (See, e.g., U.S. Pat. No. 5,219,740.) Representative retroviral vectors include but are not limited to vectors such as the LHL, N2, LNSAL, LSHL and LHL2 vectors described in e.g., U.S. Pat. No. 5,219,740, incorporated herein by reference in its entirety, as well as derivatives of these vectors. Retroviral vectors can be constructed using techniques well known in the art. See, e.g., U.S. Pat. No. 5,219,740; Mann et al. (1983) Cell 33:153-159.

Adenovirus based systems have been developed for gene delivery and are suitable for delivery according to the methods described herein. Human adenoviruses are double-stranded DNA viruses which enter cells by receptor-mediated endocytosis. These viruses are particularly well suited for gene transfer because they are easy to grow and manipulate and they exhibit a broad host range in vivo and in vitro.

Adenoviruses infect quiescent as well as replicating target cells. Unlike retroviruses which integrate into the host genome, adenoviruses persist extrachromosomally thus minimizing the risks associated with insertional mutagenesis. The virus is easily produced at high titers and is stable so that it can be purified and stored. Even in the replication-competent form, adenoviruses cause only low level morbidity and are not associated with human malignancies. Accordingly, adenovirus vectors have been developed which make use of these advantages. For a description of adenovirus vectors and their uses see, e.g., Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; Rich et al. (1993) Human Gene Therapy 4:461-476.

AAV Expression Vectors

In a preferred embodiment, the viral vectors used in the subject methods are AAV vectors. By an "AAV vector" is meant a vector derived from an adeno-associated virus serotype, including without limitation, AAV-1, AAV-2, AAV-3, AAV-4, AAV-5, AAVX7, etc. Typical AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. An AAV vector includes at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging. For more on various AAV serotypes, see for example Cearley et al., Molecular Therapy, 16:1710-1718, 2008, which is expressly incorporated herein in its entirety by reference.

AAV expression vectors may be constructed using known techniques to provide as operatively linked components in the direction of transcription, control elements including a transcriptional initiation region, the DNA of interest and a transcriptional termination region. The control elements are selected to be functional in a thalamic and/or cortical neuron. Additional control elements may be included. The resulting construct which contains the operatively linked components is bounded (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, e.g., Kotin, R. M. (1994) Human Gene Therapy 5:793-801; Berns, K. I. "Parvoviridae and their Replication" in Fundamental Virology, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

Suitable DNA molecules for use in AAV vectors will include, for example, a gene that encodes a protein that is defective or missing from a recipient subject or a gene that encodes a protein having a desired biological or therapeutic effect (e.g., an enzyme, or a neurotrophic factor). The artisan of reasonable skill will be able to determine which factor is appropriate based on the neurological disorder being treated.

The selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In one embodiment, a promoter that is operable in thalamic neurons is used.

In one embodiment, a promoter that is operable in cortical neurons is used.

In one embodiment, a promoter that is operable in both thalamic and cortical neurons is used.

For purposes of the present invention, both heterologous promoters and other control elements, such as CNS-specific and inducible promoters, enhancers and the like, will be of particular use. Examples of heterologous promoters include the CMB promoter. Examples of CNS-specific promoters include those isolated from the genes from myelin basic protein (MBP), glial fibrillary acid protein (GFAP), and neuron specific enolase (NSE). Examples of inducible promoters include DNA responsive elements for ecdysone, tetracycline, hypoxia and aufin.

The AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM $MgCl_2$, 10 mM DTT, 33 μg/ml BSA, 10 mM-50 mM NaCl, and either 40 μM ATP, 0.01-0.02 (Weiss) units T4 DNA ligase at 0° C. (for. "sticky end" ligation) or 1 mM ATP, 0.3-0.6 (Weiss) units T4 DNA ligase at 14° C. (for "blunt end" ligation). Intermolecular "sticky end" ligations are usually performed at 30-100 μg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods. See, e.g., Edge, Nature (1981) 292:756; Nambair et al. Science (1984) 223:1299; Jay et al. J. Biol. Chem. (1984) 259:6311.

In order to produce rAAV virions, an AAV expression vector is introduced into a suitable host cell using known techniques, such as by transfection. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Particularly suitable transfection methods include calcium phosphate co-precipitation (Graham et al. (1973) Virol. 52:456-467), direct micro-injection into cultured cells (Capecchi, M. R. (1980) Cell 22:479-488), electroporation (Shigekawa et al. (1988) BioTechniques 6:742-751), liposome mediated gene transfer (Mannino et al. (1988) BioTechniques 6:682-690), lipid-mediated transduction (Feigner et al. (1987) Proc. Natl. Acad. Sci. USA 84:7413-7417), and nucleic acid delivery using high-velocity microprojectiles (Klein et al. (1987) Nature 327:70-73).

For the purposes of the invention, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL 1573) are preferred in the practice of the present invention. Particularly, the human cell line 293 is a human embryonic kidney cell line that has been transformed with adenovirus type-5 DNA fragments (Graham et al. (1977) J. Gen. Virol. 36:59), and expresses the adenoviral E1a and E1b genes (Aiello et al. (1979) Virology 94:460). The 293 cell line is readily transfected, and provides a particularly convenient platform in which to produce rAAV virions.

AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) J. Virol. 63:3822-3828; and McCarty et al. (1991) J. Virol. 65:2936-2945. A number of other vectors have been described which encode Rep and/or Cap expression products. See, e.g., U.S. Pat. No. 5,139,941.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) Current Topics in Microbiol. and Immunol. 158:97-129; and Kotin, R. M. (1994) Human Gene Therapy 5:793-801. Suitable homologues of the AAV rep coding region include the human herpesvirus 6 (HHV-6) rep gene which is also known to mediate AAV-2 DNA replication (Thomson et al. (1994) Virology 204:304-311).

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. For a description of the AAV cap coding region, see, e.g., Muzyczka, N. and Kotin, R. M. (supra).

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) J. Virol. 63:3822-3828; and McCarty et al. (1991) J. Virol. 65:2936-2945. A number of other vectors have been described which encode Rep and/or Cap expression products. See, e.g., U.S. Pat. No. 5,139,941.

Both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the hygromycin B resistance gene (encoding Aminoglycoside phosphotranferase (APH)) that allows selection in mammalian cells by conferring resistance to G418 (available from Sigma, St. Louis, Mo.). Other suitable markers are known to those of skill in the art.

AAV Accessory Functions

The host cell (or packaging cell) must also be rendered capable of providing non AAV derived functions, or "accessory functions," in order to produce rAAV virions. Accessory functions are non AAV derived viral and/or cellular functions upon which AAV is dependent for its replication.

Thus, accessory functions include at least those non AAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

Particularly, accessory functions can be introduced into and then expressed in host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) J. Virol 40:241-247; McPherson et al. (1985) Virology 147:217-222; Schlehofer et al. (1986) Virology 152:110-117.

Alternatively, accessory functions can be provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, transposon or cosmid. Accessory vectors can also be in the form of one or more linearized DNA or RNA fragments which, when associated with the appropriate control elements and enzymes, can be transcribed or expressed in a host cell to provide accessory functions. See, for example, International Publication No. WO 97/17548, published May 15, 1997.

Nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. See, e.g., Carter, B. J. (1990) "Adeno-Associated Virus Helper Functions," in CRC Handbook of Parvoviruses, vol. I (P. Tijssen, ed.), and Muzyczka, N. (1992) Curr. Topics. Microbiol. and Immun. 158:97-129. Specifically, early adenoviral gene regions E1a, Eta, E4, VAI RNA and, possibly, E1b are thought to participate in the accessory process. Janik et al. (1981) Proc. Natl. Acad. Sci. USA 78:1925-1929. Herpesvirus-derived accessory functions have been described. See, e.g., Young et al. (1979) Prog. Med. Virol. 25:113. Vaccinia virus-derived accessory functions have also been described. See, e.g., Carter, B. J. (1990), supra., Schlehofer et al. (1986) Virology 152:110-117.

As a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the host cell using a variety of conventional purification methods, such as CsCl gradients. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions are then ready for use for DNA delivery to the CNS.

For in vivo delivery, the rAAV virions will be formulated into pharmaceutical compositions.

Therapeutic Nucleic Acids and Encoded Proteins

Therapeutic nucleic acids include nucleic acids that are directly therapeutic as well as nucleic acids that give rise to therapeutic agents, e.g., therapeutic proteins.

Therapeutic proteins include biologically active variants and fragments. The term "variant" as used herein includes polypeptides in which amino acids have been deleted from ("deletion variants"), inserted into ("addition variants"), or substituted for ("substitution variants"), residues within the amino acid sequence of a parent protein. Such variants are prepared by introducing appropriate nucleotide changes into the DNA encoding the polypeptide. It will be appreciated by those skilled in the art that many combinations of deletions, insertions, and substitutions can be made provided that the final molecule is biologically active.

Therapeutic proteins include, but are not limited to enzymes; growth factors, including neurotrophins; hormones; immunomodulatory peptides and proteins, including cytokines; and neuromodulatory peptides.

In a preferred embodiment, a therapeutic protein of the invention is selected from the group consisting of NGF, BDNF, NT-3, NT-4/5, NT-6, GDNF, CNTF, LIF, b-FGF, neurturin, persephin, artemin, TGFα, TGFβ, IGF-2, PDGF, EGF, cardiotropin, EGF, IGF, VEGF, Sonic hedgehog (SHH), BMP, FGF20, VIP, PDGF, pleiotrophin (PTN), and HGF.

In one embodiment, the therapeutic protein is capable of being produced in the thalamus and released in the cerebral cortex.

The type of therapeutic nucleic acid used will depend on the neurological disorder being treated. It will be apparent to the reasonably skilled artisan which neurological disorders are suitable for treatment by the present methods based on cortical pathology and neuroanatomical connectivity.

For example, gene therapy may be done using a viral particle that provides for the production of an enzyme that is deficient in the neurological disorder (e.g., Canavan disease). Alternatively, gene therapy may be done using a viral particle that provides for the production of a neurotrophin, e.g., NGF, to sustain a population of neurons that is compromised in the neurological disorder, e.g., neurons of the basal forebrain, which innervate the cortex, in Alzheimer's disease.

Alternative therapeutic agents may be used in the subject invention, including but not limited to siRNA and other means for gene silencing.

Pharmaceutical Compositions and Administration

Pharmaceutical compositions will comprise a therapeutically effective amount of the therapeutic agent of interest, i.e., an amount sufficient to reduce or ameliorate symptoms of the disorder in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Artificial CSF may also be used in the subject methods. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

The optimal pharmaceutical formulation will be determined by one skilled in the art. The final dosage regimen involved in a method for treating the above-described conditions will be determined by the attending physician, considering various factors which modify the action of drugs. As studies are conducted, further information will emerge regarding the appropriate dosage levels for the treatment of various neurological disorders.

The pharmaceutical composition may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected agent without causing any undesirable biological effects or interacting in a deleterious manner with any of the other components of the pharmaceutical composition in which it is contained.

In a preferred embodiment, a pharmaceutical composition of the invention is locally deliverable into the CNS of a subject by CED.

In one embodiment, the pharmaceutical composition comprises a facilitating agent. A facilitating agent is capable of further facilitating the delivery of infusate to target tissue. Facilitating agents are especially preferred when the therapeutic agent is a therapeutic protein.

Once the pharmaceutical composition has been formulated, it may be stored in sterile vials as a solution, suspension, gel, emulsion, solid, or dehydrated or lyophilized powder. Such formulations may be stored either in a ready to use form or in a form, e.g. lyophilized, requiring reconstitution prior to administration.

As is apparent to those skilled in the art in view of the teachings of this specification, an effective amount of therapeutic agent which must be added can be empirically determined. Administration can be effected in one dose, continuously or intermittently throughout the course of treatment. An "effective amount" is an amount sufficient to effect beneficial or desired results. An effective amount can be administered in one or more administrations, applications or dosages.

In embodiments wherein the therapeutic agent delivered to the thalamus is a therapeutic protein, more than one dose is preferred. See for example U.S. Ser. No. 11/740,124, filed Apr. 25, 2007, which is incorporated herein by reference in its entirety.

The terms "subject", "individual" or "patient" are used interchangeably herein and refer to large mammals, preferably primates, and most preferably humans, and does not include small mammals such as rodents.

Combination therapies are contemplated. For example, in methods involving viral vectors, it should be understood that more than one transgene can be expressed by the delivered viral vector. Alternatively, separate vectors, each expressing one or more different transgenes, can also be delivered to the CNS. Furthermore, it is also contemplated that the therapeutic agents, including viral vectors, delivered by the methods of the present invention be combined with other suitable compositions and therapies.

Delivery Devices

Any convection-enhanced delivery device may be appropriate for delivery of therapeutic agents. In a preferred embodiment, the device is an osmotic pump or an infusion pump. Both osmotic and infusion pumps are commercially available from a variety of suppliers, for example Alzet Corporation, Hamilton Corporation, Alza, Inc., Palo Alto, Calif.). Typically, a therapeutic agent is delivered via CED devices as follows. A catheter, cannula or other injection device is inserted into CNS tissue in the chosen subject. In view of the teachings herein, one of reasonable skill in the art could readily determine the appropriate coordinates for insertion. Positioning may be conducted by using anatomical maps obtained by CT and/or MRI imaging of the subject's brain to help guide the injection device to the chosen target. Alternatively, iMRI and real-time imaging of delivery may be done.

Exemplary pump systems for use in the subject invention include the implantable systems described in U.S. Pat. Nos. 7,351,239; 7,341,577; 6,042,579; 5,735,815 and 4,692,147.

An exemplary catheter for use in the subject invention is described in PCT/US08/64011. Other exemplary catheters are described herein.

All citations are expressly incorporated herein in their entirety by reference.

EXPERIMENTAL

Widespread Transgenic Protein Expression after Intra-Thalamic AAV2 Vector Delivery.—FIGS. 1-4

Figure 2:
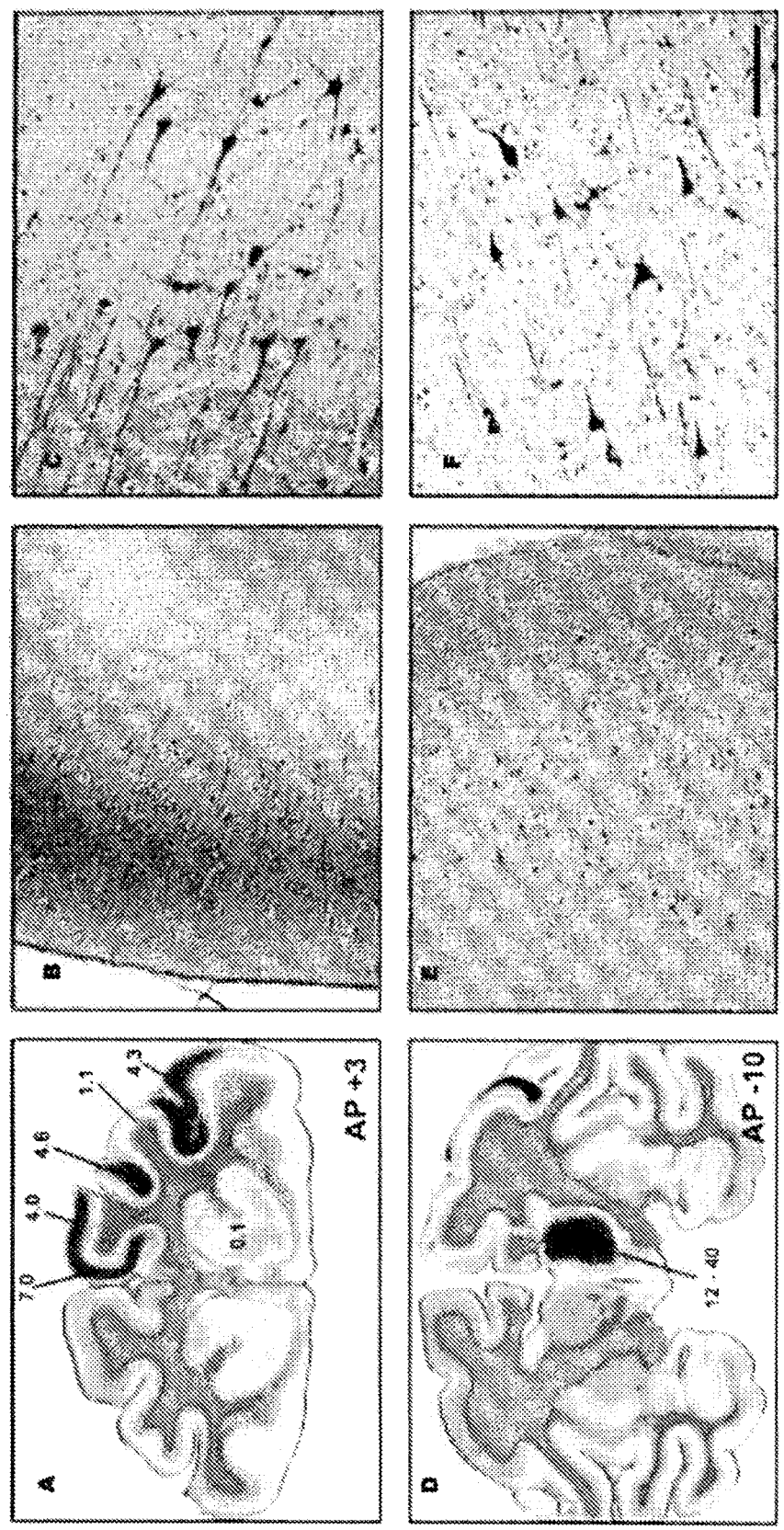
FIG. 2. Level of GDNF expression after infusion of AAV2-GDNF into right thalamus. (A-F) Pseudo-color images of GDNF IHC stained sections showing the gradients of GDNF distribution in both the thalamus and cortex. Blue represents the highest intensity of DAB staining and red the lowest intensity. Numbers in panels A and D represent the level of GDNF protein (µg GDNF per mg total protein) is different areas of the brain measured from an adjacent tissue block. (B, C, E, F) Higher magnification of the cortex shows the high intensity of GDNF staining in lamina III/IV and high cytoplasmic presence of GDNF in lamina V/VI pyramidal neurons. Anterior/Posterior distance in mm from bregma. Scale bar: 10 mm (A, D), 500 μm (B, E), 100 μm (C, F).
Figure 3:
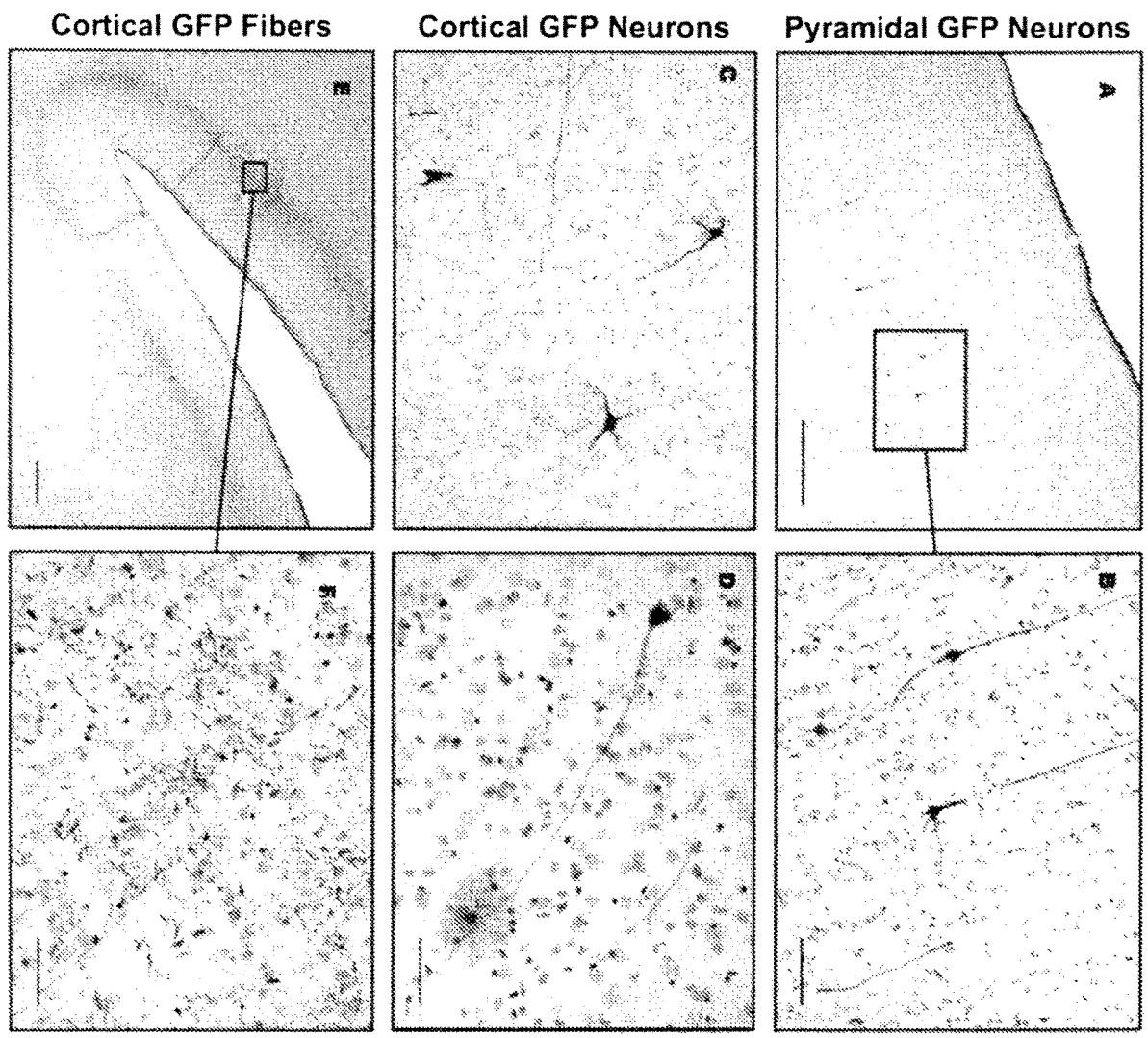
FIG. 3. Cortical expression of GFP after infusion of AAV2-GFP to the left thalamus. Individual GFP-immunopositive neurons were found within different areas of the cortex. (A, B) Cortical pyramidal neurons were the predominant type of GFP-positive neuron. Neurons that did not have pyramidal morphology were also found in the cortex including (C) basket-like neurons and (D) glia-like cells. (E, F) Extensive GFP-positive fiber networks were also found in the frontal cortex. Scale bars: 500 μm (A, E) 100 μm (B, C), 50 μm (D, F).

AAV2-GDNF drives abundant secretion of glial-derived neurotrophic factor (GDNF) from transduced neurons that can be visually detected by immunohistochemistry and quantified by ELISA of tissue extracts. After infusion of AAV2-GDNF into the thalamus by convection-enhanced delivery, extensive GDNF-immunopositive staining was detected in the frontal cortex ipsilateral to the infusion site. As shown in FIG. 1, the expression of GDNF extended from prefrontal association cortical areas (Cortical Areas 9 and 10) through the frontal eye-fields (Area 8), pre-motor cortex (Area 6), primary somatosensory cortical areas (Areas 3, 1 and 2) to primary motor cortex (Area 4), and included expression in the cingulate cortex (Areas 23, 24, 32) and Broca's area (Area 44, 45). GDNF expression in the cortex was localized to the gray matter with a distinct lack of GDNF-positive staining in the underlying white matter tracts. A similar pattern was found in the thalamus where GDNF expression was also contained within the gray matter bounds of the infusion targeted thalamic nuclei with no evidence of infusion related "leakage" or reflux of the AAV2-GDNF vector into non-targeted areas. No GDNF staining was found in the contralateral hemisphere in any of the sections analyzed. In addition to the intense staining of individual neuronal cell bodies and cellular processes, GDNF staining was observed across multiple layers of the frontal cortex with an intensity gradient that was highest in cortical Layers III and IV (FIG. 2).

The macroscopically evident GDNF staining of large cortical regions correlated with the presence of GDNF-positive neuronal fibers and cell bodies; however, the overall intensity of immunostaining did not reflect the actual number of GDNF-positive neurons in a specific area when examined microscopically with extensive non-cellular staining observed indicative of secreted GDNF. Most GDNF-positive neurons within the cortex were identified morphologically as pyramidal neurons located in cortical Layer V/VI with axonal projections into the overlying layers (FIG. 1E, F). Density of GDNF-positive neurons was particularly high in the anterior cortex including prefrontal cortical area 8 where large numbers of non-pyramidal neurons were observed in Layers II-IV (FIG. 1A-C).

The level of GDNF protein present in the thalamus, striatum and various cortical areas was quantified six months after AAV2-GDNF delivery. GDNF in the vector-infused thalamus ranged from 12 to 40 ng per mg protein (contralateral hemisphere <0.6 ng) and in the ipsilateral frontal cortex from 1 to 7 ng (no GDNF was detected in the contralateral cortex). Values in FIG. 2 indicate the approximate correlation of GDNF quantification with GDNF immunostaining from an adjacent coronal tissue block.

Thalamocortical Trafficking of AAV2 Vector and Transduction of Cortical Neurons.

Cytoplasmic expression and accumulation of green fluorescent protein (GFP) in transduced cells after AAV2-GFP delivery was utilized to assess the localization of transduced neurons after thalamic infusion in NHP's. GFP expression was analyzed in both the thalamus and frontal cortex to investigate correlations between the distribution of AAV2 vector in the thalamus and the transduction of neurons in specific regions of the cortex indicative of thalamocortical axonal trafficking of AAV2 vectors.

Figure 4:
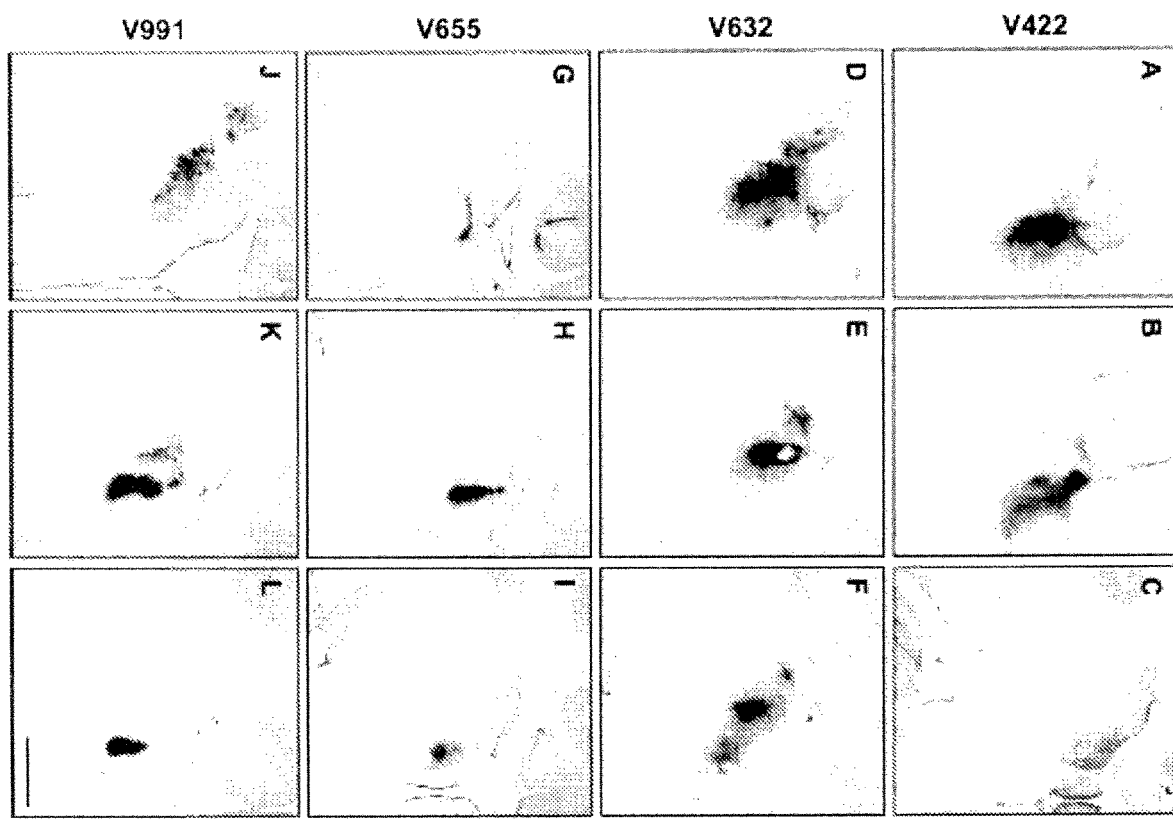
FIG. 4. GFP immunostaining in the thalamus after CED of AAV2-GFP of the animals shown in FIG. 3. Specific thalamic nuclei were transduced that resulted in corresponding cortical delivery of GFP.

Distribution of AAV2-GFP infusion within the thalamus was assessed in four NHP's (ID numbers V422, V632, V655 and V991) with respect to specific thalamic nuclei containing GFP-immunopositive neurons. Due to small differences in cannula positioning, each animal showed some discrepancy in the thalamic distribution of GFP staining (FIG. 4). In summary, AAV2-GFP transduction within the thalamus was most extensive in monkey V422 with GFP expression throughout the ventral lateral, ventral anterior and mediodorsal nuclei extending rostrally into the anterior nucleus. Monkey V632 showed a more posterior infusion with GFP-positive neurons extending from ventral anterior to ventral posterior nuclei. Monkey V655 had restricted distribution of GFP-positive neurons, mainly contained within the mediodorsal and ventral lateral nuclei. Monkey V991 received a slightly more lateral infusion of AAV2-GFP resulting in transduction of the ventral lateral and ventral anterior nuclei with GFP expression also observed in the internal capsule. Evidence of vector leakage/reflex back up the cannula tract into the lateral ventricle was seen in V655 and V991, but not in the other two animals. This reflux resulted in a smaller area of transduction in the thalamus.

Immunohistochemical analysis of the frontal cortex for specific regions of the frontal cortex in which GFP-positive neuronal cell bodies and processes were clearly distinguishable (FIG. 3A, B). Most GFP-positive neurons were identified as pyramidal neurons located in Layer V/VI. However, other GFP-positive cells were found in smaller numbers with the morphology of basket neurons and glia (FIG. 3E, F). Additionally, we also observed areas in which GFP staining was localized to fibers in Layer IV (FIG. 3C, D). In contrast to the AAV2-GDNF treated monkeys, all transgenic protein (GFP) staining was clearly localized to neuronal structures indicating intracellular accumulation of GFP specifically within neurons compared to the secretion and extracellular diffusion of GDNF.

Systematic scanning of GFP-immunostained coronal sections from the four monkeys, identified specific regions of the frontal cortex that contained GFP-positive neurons. As with AAV-GFP transduction of thalamic neurons, distribution of GFP-positive cells in the cortex was slightly different for each monkey (Table 1). The main region in which the majority of GFP-positive neurons were consistently found was the secondary motor cortex (Area 6) and frontal eye fields (Area 8). The anterior cingulate cortex (Areas 24 and 32) also contained GFP-positive neurons in each animal. In addition GFP-positive neurons were also found in other cortical areas including primary motor cortex (Area 4), somatosensory cortex (Areas 3 and 2), posterior cingulate cortex (Areas 23 and 31) and Broca's area (Areas 44 and 45). As summarized in Table 1, monkey V422 had considerable distribution of GFP-positive neurons in the frontal eye fields and Broca's area. Monkey V632 was the only animal with GFP expression in the primary somatosensory cortex but lacked any expression in Broca's area. Monkey V655 displayed diffuse distribution of GFP-positive cortical neurons across most of the cortical areas analyzed. Monkey V991 had restricted expression with GFP-positive neurons only found in the anterior cingulate cortex, secondary motor cortex and frontal eye fields. No GFP-positive cells were ever observed in the hemisphere contralateral to the infusion site.

Translocation of GDNF from Cortex to Tertiary CNS Site—the Basal Forebrain

The level of GDNF protein present in the basal forebrain was quantified six months after AAV2-GDNF delivery using the methods described herein. The subject was that represented in FIG. 2. The results were: treated side=0.91 ng GDNF/mg protein; contralateral side=0.45 ng GDNF/mg protein. The results establish that therapeutic agent delivered via the thalamus to a cortical population can be transported to a tertiary neuronal population connected to the cortex.

Delivery of NGF to Basal Forebrain via Transport from Cortex Following Thalamocortical Gene Delivery in Non-Human Primate Model of Alzheimer's Disease An AAV2 particle comprising a therapeutic nucleic acid encoding NGF is prepared. The AAV2 particle is delivered to the thalamus of an aged non-human primate, as an art-recognized model of Alzheimer's disease. See, for example, Price et. al., "Aged non-human primates: an animal model of age-associated neurodegenerative disease", Brain Pathol., 1:287-296, 1991. AAV2 is preferably delivered to one or more of the anterior nucleus, medio-dorsal nucleus, ventral anterior nucleus, ventral lateral nucleus, and ventral posterior nucleus, with the ventral nuclei being preferred. AAV2 particles transduce thalamic neurons, and NGF is translocated to the cortex. AAV2 particles are also translocated to the cortex, including the cingulate cortex, transduce neurons therein, and produce NGF in the cortex. NGF and/or AAV2 particles are translocated from the cortex to the basal forebrain, and support the survival and/or cholinergic phenotype of neurons therein.

Delivery of NGF to Basal Forebrain via Transport from Cortex Following Thalamocortical Gene Delivery in Alzheimer's Disease An AAV2 particle comprising a therapeutic nucleic acid encoding NGF is prepared. The AAV2 particle is delivered to the thalamus of an Alzheimer's patient, preferably to one or more of the anterior nucleus, medio-dorsal nucleus, ventral anterior nucleus, ventral lateral nucleus, and ventral posterior nucleus, with the ventral nuclei being preferred. AAV2 particles transduce thalamic neurons, and NGF is translocated to the cortex. AAV2 particles are also translocated to the cortex, including the cingulate cortex, transduce neurons therein, and produce NGF in the cortex. NGF and/or AAV2 particles are translocated from the cortex to the basal forebrain, and support the survival and/or cholinergic phenotype of neurons therein.

By this method, trophic support in the form of NGF is delivered to the basal forebrain via its physiological target, i.e., the cortex. Native basal forebrain innervation to the cortex is strengthened (e.g., sprouting may be increased) rather than diverted as it might be by neurotrophin supply from auxiliary non-physiological sites, and survival and/or cholinergic phenotype are supported.

Discussion

We infused AAV2-GDNF into the thalamus and observed high concentrations of GDNF in the frontal cortex. GDNF in the cortex appeared to be largely localized to lamina III and IV where the majority of thalamocortical axons are known to innervate (3, 4), indicating secretion from the thalamic terminals. In addition to the extracellular GDNF staining, many lamina V/VI pyramidal neurons within the same cortical areas also contained GDNF, suggesting transduction of cortical neurons by AAV2-GDNF. Many of the GDNF-positive neurons in the frontal cortex were located over 20 mm from the AAV2-GDNF infusion site, a distance significantly greater than explicable solely by vector infusion. With no significant GDNF expression detected outside the cortex and thalamus, this specific transportation between the thalamus and cortex suggested axonally mediated transportation of both GDNF protein and AAV2 vector.

Axonal trafficking of AAV2 was further investigated with AAV2-GFP since, unlike GDNF, GFP remains cytoplasmic and is therefore indicative of direct cellular transduction. Cytoplasmic staining of cortical neurons for GDNF could theoretically have resulted from the uptake of secreted GDNF. By mapping the localization of GFP-positive neurons in the frontal cortex of each monkey and analyzing this transduction of cortical cells in conjunction with the observed thalamic distribution of AAV2-GFP vector for each infusion, we were able to infer some of the known topographical organization of the thalamocortical projections (5, 6) suggesting active transportation of AAV2 vectors along single axonal projections. In the most restricted thalamic infusion, GFP was largely contained within neurons of the medio-dorsal and ventral lateral thalamic nuclei. Therefore, with this restricted infusion as a starting reference it was assumed that GFP-positive neurons, located in the secondary motor cortex and prefrontal cortex of each subject, resulted at least in part from AAV2 vector transport along axonal projections connecting the medial thalamic nucleus and secondary motor cortex. Neurons of the medial nuclear group have previously been shown to send efferent projections to the frontal cortex coherent with these current observations (3, 7). A slightly more anterior infusion that transduced the ventral anterior and ventral lateral thalamic nuclei resulted in a very similar pattern of cortical GFP expression to the medial thalamic infusion with GFP-positive cells observed in the secondary motor cortex, cingulate cortex and frontal eye fields. Although the thalamocortical projections are very topographically organized, there is considerable overlap in cortical connections especially from adjacent thalamic structures. Spread of AAV2-GFP transduction into the anterior thalamic nucleus generated GFP-positive neurons in Broca's area, whereas a more caudal spread to ventral posterior nucleus resulted in GFP-positive neurons in the primary somatosensory cortex and primary motor cortex.

The correlation between topological organization of thalamocortical projections and the observed areas of cortical transduction suggest that transfer of AAV2 to the cortex is mediated by anterograde axonal transportation. Possible anterograde transport of other AAV serotypes 1 and 9 was recently observed in the mouse brain (12). However, reciprocal projections and the small size of the mouse brain prevented conclusive determination of transport mechanisms.

Methods and Materials

FIGS. 1-4

Surgical Delivery

Recombinant AAV2 vectors containing either human GDNF cDNA (AAV2-GDNF) or GFP cDNA (AAV2-GFP) under the control of cytomegalovirus promoter were infused into the right thalamus of six adult Rhesus monkeys by convection enhanced delivery (CED) protocol we have previously described (13). All experimentation was performed according to the National Institutes of Health guidelines and to the protocols approved by the Institutional Animal Care and Use Committee at the University of California San Francisco.

Production of AAV

Recombinant AAV2-GDNF (human Glia-derived Neurotrophic Factor) was constructed by a triple transfection technique (14, 15). AAV2-GFP was produced in insect cells with a recombinant baculovirus (16). Both vectors underwent CsCl gradient centrifugation to remove empty capsids. AAV2-GFP and AAV2-GDNF were obtained at a stock concentration of $1.0 \times 10^{13}$ and $1.1 \times 10^{13}$ vector genomes per ml in phosphate-buffered saline (pH 7.4) and Pluronic F-68 (0.001% v/v).

Immunohistochemistry

Immunostaining with antibodies against GDNF (1:500, AF-212-NA, R&D Systems) and GFP (1:500, AB3080, Chemicon) was performed on Zamboni fixed 40-µm coronal sections covering the entire frontal cortex and extending in a posterior direction to the level of the thalamus. The localization of GDNF and GFP immunopositive neurons was analyzed with reference to The Rhesus Monkey Brain in Stereotactic Coordinates (17) to identify specific areas of immunostaining in the cortex and thalamus.

GDNF Protein ELISA

Tissue punches from 3-mm coronal blocks of fresh frozen tissue were taken from a number of cortical, thalamic and striatal regions of an AAV2-GDNF infused monkey as indicated on GDNF immunostained sections from adjacent tissue blocks shown in FIG. 1. The level of GDNF protein expressed was quantified by ELISA assay with a commercial GDNF ELISA kit (Emax GDNF ELISA, Promega, Wis.) specific for human GDNF.

TABLE 1

Relative distribution of GFP-positive neurons in the cortex

| Monkey ID number | Thalamic Nuclei Cortical Area | Prefrontal Cortex 9/10/46 | Broca's Area 44/45 | Frontal Eye Fields 8 | Secondary Motor Cortex 6 | Anterior Cingulate Cortex 24/32 | Somatosensory Cortex 3/1/2 | Primary Motor Cortex 4 | Posterior Cingulate Cortex 23/31 |
|---|---|---|---|---|---|---|---|---|---|
| V422 | AN VA MD | ** | *** | *** | *** | ** |  | * |  |
| V632 | VA VL VP |  |  | ** | *** | ** | ** | ** | ** |
| V655 | VL MD | *** | * | *** | *** | ** |  | * | * |
| V991 | VA VL | * | * | ** | ** | * |  |  |  |

Representation of GFP-positive neuronal distribution in the cortex ipsilateral to the thalamic infusion. Relative distribution of GFP-positive cortical neurons:
*** majority of neurons;
** smaller numbers of neurons;
* few isolated neurons.
Abbreviations: AN Anterior nucleus; MD medio-dorsal nucleus; VA ventral anterior nucleus; VL ventral lateral nucleus; VP ventral posterior nucleus.

REFERENCES—FIGS. 1-4

1. Vite C H, et al. (2005) Effective gene therapy for an inherited CNS disease in a large animal model. Ann Neurol 57(3):355-364.
2. Vito C H. Passini M A, Haskins M E, & Wolfe J H (2003) Adeno-associated virus vector-mediated transduction in the cat brain. Gene Ther 10(22):1874-1881.
3. Giguere M & Goldman-Rakic P S (1988) Mediodorsal nucleus: areal, laminar, and tangential distribution of afferents and efferents in the frontal lobe of rhesus monkeys. J Comp Neurol 277(2):195-213.
4. Jacobson S & Trojanowski J Q (1975) Corticothalamic neurons and thalamocortical terminal fields: an investigation in rat using horseradish peroxidase and autoradiography. Brain Res 85(3):385-401.
5. Kievit J & Kuypers H G (1977) Organization of the thalamo-cortical connexions to the frontal lobe in the rhesus monkey. Exp Brain Res 29(3-4):299-322.
6. Brysch W, Brysch I, Creutzfeldt O D, Schlingensiepen R, & Schlingensiepen K H (1990) The topology of the thalamo-cortical projections in the marmoset monkey (Callithrix jacchus). Exp Brain Res 81(1):1-17.
7. Goldman-Rakic P S & Porrino L J (1985) The primate mediodorsal (MD) nucleus and its projection to the frontal lobe. J Comp Neurol 242(4):535-560.
8. Kaspar B K, et al. (2002) Targeted retrograde gene delivery for neuronal protection. Mol Ther 5(1):50-56.
9. Boulis N M, et al. (2003) Adeno-associated viral vector gene expression in the adult rat spinal cord following remote vector delivery. Neurobiol Dis 14(3):535-541.
10. Kaspar B K, Llado J, Sherkat N, Rothstein J D, & Gage F H (2003) Retrograde viral delivery of IGF-1 prolongs survival in a mouse ALS model. Science 301(5634):839-842.
11. Killackey H P & Sherman S M (2003) Corticothalamic projections from the rat primary somatosensory cortex. J Neurosci 23(19):7381-7384.
12. Cearley C N & Wolfe J H (2007) A single injection of an adeno-associated virus vector into nuclei with divergent connections results in widespread vector distribution in the brain and global correction of a neurogenetic disease. J Neurosci 27(37):9928-9940.
13. Bankiewicz K S, et al. (2000) Convection-enhanced delivery of AAV vector in parkinsonian monkeys; in vivo detection of gene expression and restoration of dopaminergic function using pro-drug approach. Exp Neurol 164(1):2-14.
14. Matsushita T, et al. (1998) Adeno-associated virus vectors can be efficiently produced without helper virus. Gene Ther 5(7):938-945.
15. Wright J F, Qu G, Tang C, & Sommer J M (2003) Recombinant adeno-associated virus: formulation challenges and strategies for a gene therapy vector. Curr Opin Drug Discov Devel 6(2):174-178.
16. Urabe M, Ding C, & Kotin R M (2002) Insect cells as a factory to produce adeno-associated virus type 2 vectors. Hum Gene Ther 13(16):1935-1943.
17. Paxinos G, Huang X F, & Toga A W (2000) The rhesus monkey brain in stereotaxic coordinates (Academic Press, San Diego).

Example

Wide-Spread Enzyme Expression after Intra-Thalamic AAV2-Vector Delivery

Methods and Materials

FIGS. 5-11

Non-Human Primate (NHP) Subjects

Four NHP (Cynomolgus) were used in this study and were randomized to a 5-week, (n=2) or 9-week survival (n=2) group, based on the time after they received their last infusion treatment. No differences in body weight, neurological deficits or adverse clinical symptoms were observed during the course of the study. All animal handling and procedures were carried out in accordance with the UCSF institutional animal care and use committee. NHP received two treatments, one with Gadoteridol only (NHP=4, 3 thalamic and 2 brainstem infusions) and one with AAV2-hASM-HA/Gadoteridol (NHP=4, 8 thalamic and 4 brainstem infusions).

Adeno-Associated Virus (AAV) Vector Construction

An AAV shuttle plasmid encoding human acidic sphingomyelinase (hASM), previously described [17], was modified by inclusion at the 3' end of the ASM cDNA of a sequence that generated a C-terminal synthetic hemagglutinin epitope derived from viral hemagglutinin in order to facilitate immunodetection of transgene expression in NHP brain. This shuttle plasmid was then used to manufacture [23] AAV2-hASM-HA (1.0×10e12 vg/mL) at the Vector Core at Children's Hospital of Philadelphia (CHOP).

AAV2-hASM-HA Infusion

Figure 5:
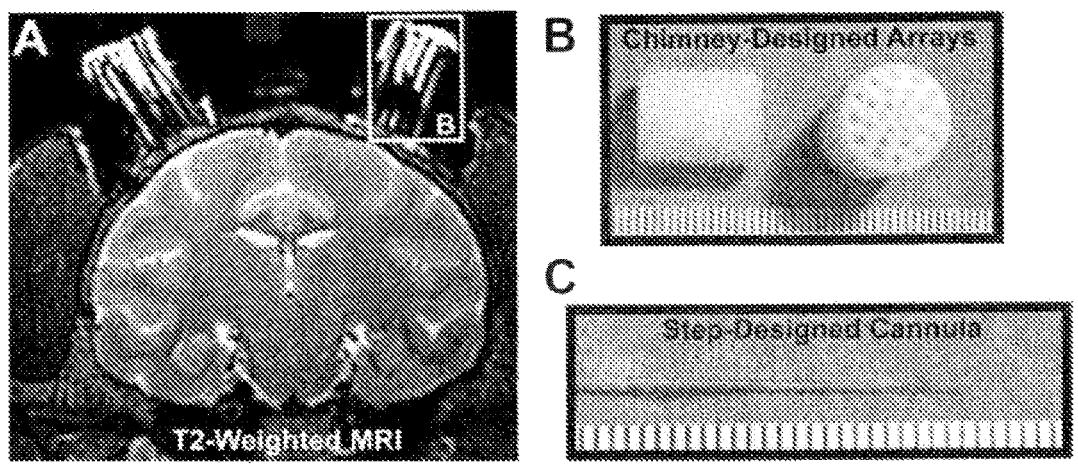
FIG. 5. Array CED Components for CNS Parenchymal Infusate delivery. (A) T2-weight MR image showing NHP brain with chimney-array positioned on skull surface (B). These chimney-designed arrays are utilized for securely inserting reflux resistant, step-designed cannulas (C) for efficient infusate delivery into the CNS parenchyma.

All NHP received a baseline MRI prior to surgery to visualize anatomical landmarks and to generate stereotactic coordinates of the proposed infusion target sites. NHP underwent stereotactic placement of the MRI-compatible plastic guide cannula array (12 mm diameter×14 mm height containing 27 access holes) for CED into the thalamus and brainstem (FIG. 5). Each guide cannula array was secured to the skull with plastic screws and dental acrylic. After placement of the guide cannula array, animals recovered for at least 2 weeks before initiation of infusion procedures. On the day of infusion, animals were anesthetized with isoflurane (Aerrane; Ohmeda Pharmaceutical Products Division, Liberty Corner, N.J.). Each animal's head was then placed in an MRI-compatible stereotactic frame, and a baseline MRI was performed. Vital signs, such as pulse and $PO_2$, were monitored throughout the procedure. Briefly, the infusion system consisted of a fused silica reflux-resistant cannula [19, 24] that was connected to a loading line (containing the infusate [i.e. Gd only or AAV/Gd]), an infusion line filled with mineral oil, and another infusion line with trypan blue solution. A 1-ml syringe, the barrel filled with trypan blue solution, was mounted onto a MRI-compatible infusion pump (Harvard Bioscience, Holliston, Mass.) that regulated the flow of fluid through the delivery cannula. Based on MRI coordinates, the cannula was inserted into the targeted region of the brain through the previously placed guide cannula array. The length of each infusion cannula was measured to ensure that the distal tip extended 3 mm beyond the cannula step. This created a stepped design that was proximal to the tip of the cannula, maximizing fluid convection during CED while minimizing reflux along the cannula tract. We maintained positive pressure in the infusion cannula during its insertion into the brain. After securing placement of the infusion cannula, the CED procedures were initiated with the acquisition of MRI data in near real time (real-time convective delivery, RCD). We used the same infusion parameters for every NHP infused throughout the study except that the volume infused ranged from 33 to 199 μL, more specifically infused volumes for the thalamus ranged from 33-169 μL and for the brainstem ranged from 125-1994. Infusion rates were as follows: 0.1 μl/min was applied when lowering cannula to targeted area (to prevent tissue from entering the tip) and, upon reaching the target, increased at 10-min intervals to 0.2, 0.5, 0.8, 1.0, and 2.0 μl/min. Approximately 15 min after infusion, the cannula was withdrawn from the brain. Animals receiving infusions of Gadoteridol alone prior to AAV2-hASM-HA treatment were conducted approximately 4 weeks before receiving the AAV infusions. Note that all thalamic and brainstem infusions delivering AAV2-hASM-HA were conducted simultaneously during the same procedure.

Magnetic Resonance Image (MRI)

NHP were sedated with a mixture of ketamine (Ketaset, 7 mg/kg, IM) and xylazine (Rompun, 3 mg/kg, IM). After sedation, each animal was placed in a MRI-compatible stereotactic frame. The ear-bar and eye-bar measurements were recorded, and an intravenous line was established. MRI data was then obtained, after which animals were allowed to recover under close observation until able to right themselves in their home cages. MR images for CED infusions delivering Gadoteridol alone (total of 4) were acquired on a 1.5T Siemens Magnetom Avanto (Siemens AG, Munich, Germany). Three-dimensional (3D) rapid gradient echo (MP-RAGE) images were obtained with repetition time (TR)=2110 ms, echo time (TE)=3.6 ms, and a flip angle of 15°, number of excitations (NEX)=1 (repeated 3 times), matrix=240×240, field of view (FOV)=240×240×240, and slice thickness=1 mm. These parameters resulted in a 1-mm³ voxel volume. The scanning time was approximately 9 min.

MR images for CED infusions delivering AAV2-hASM-hA/Gd (total of 12) were acquired on a 1.5-T Signa LX scanner (GE Medical Systems, Waukesha, Wis.) with a 5-inch surface coil on the subject's head, parallel to the floor. Spoiled gradient echo (SPGR) images were T1-weighted and obtained with a spoiled grass sequence, a TR=2170 ms, a TE=3.8 ms, and a flip angle of 15°. The NEX=4, matrix=256×192, FOV=16 cm×12 cm, slice thickness=1 mm. These parameters resulted in a 0.391 mm³ voxel volume. Scanning time was approximately 11 min.

Tissue Processing

NHP were transcardially perfused with a PBS flush followed by 4% paraformaldehyde (PFA)/PBS, their brains harvested and sliced coronally at 6 mm thickness in a brain matrix. Brain slices were post-fixed in 4% PFA/PBS and cryoprotected in 30% sucrose. A sliding microtome (Thermo Scientific, HM 450) was used to cut brain slices to 40-μm serial sections that were then processed for histology.

Immunoperoxidase Staining

Using a monoclonal antibody against the HA tag, all NHP processed tissue was immunostained for the expression of the human transgene. Briefly, serial brain sections were immunostained for the hemagglutinin epitope (mouse anti-HA, 1:10,000; Clone 16812, Covance). Briefly, sections were washed with PBS (3×5 min) and were quenched for endogenous peroxidase activity in 1% $H_2O_2$ in PBS (20 min), then washed again in PBS as before. Sections were blocked for 30 min in Background Sniper® (Biocare Medical, BS966G) and incubated overnight with the HA primary antibody in Biocare Da Vinci green diluent (Biocare Medical, PD900). The next day, after washing sections in PBS, sections were incubated in Mach-2-mouse-HRP polymer for 1 h (Biocare Medical, MHRP520), washed in PBS and developed with DAB for 6 min (DAB Peroxidase Subtrate Kit, SK-4100, Vector Laboratories). DAB-processed sections were washed in PBS, mounted on frosted-slides and counter-stained with Cresyl violet.

Immunofluorescent Staining

Brain sections were immunostained with a cocktail of antibodies containing anti-HA (mouse monoclonal, 1:200, Covance) and either anti-Iba1 (rabbit polyclonal, 1:100, Biocare Medical) or anti-NeuN (mouse, monoclonal, 1:500, Millipore). Alternatively anti-HA (mouse monoclonal, 1:200, Covance) was used in combination with anti-S100 (rabbit polyclonal, 1:100, Biocare Medical). Briefly, sections were washed with PBS containing 0.1% Tween-20 (PBST, 3×5 min) and were quenched for endogenous peroxidase activity in 1% $H_2O_2$ in 50% ethanol (30 min), then washed again in PBST as before. Sections were blocked for 60 min in 20% normal horse serum (NHS, Jackson Immuno Research) and incubated for at least 16 h at 4° C. with each of the primary antibody cocktails in Biocare DaVinci® green diluent (Biocare Medical, PD900). After incubation with primary antibodies, sections were washed in PBST, incubated with a cocktail of secondary antibodies anti-mouse-FITC (1:200, Jackson ImmunoResearch) and anti-rabbit-TRITC (1:200, Jackson ImmunoResearch) in PBST for 1 h at room temperature, washed in PBST and wet-mounted on frosted-slides. These sections were cover-slipped with a DAPI-containing hard-set media.

Volume Infused (Vi) versus Volume of Distribution (Vd) Ratio

Vd for each thalamic and brainstem infusion was measured with OsiriX, an imaging software dedicated to DICOM images (v3.6). Briefly, regions-of-interest (ROI) defined as the areas of visualized Gd-signal on each DICOM were manually delineated with the ROI-tool. Ratios were calculated by taking the volume of the resulting 3D reconstruction of the combined infusate (either Gd only or AAV-hASM-HA/Gd) distribution (Vd) and dividing it by the Vi. To compare Vi to Vd ratios for repeated infusions, Vd was measured on DICOM series at equivalent Vi.

Area of HA Immunostaining Transferred to MR Images

The transference of HA immunostained areas was conducted by first scanning (Epson 1660 photo scanner at 300 dpi) all histology processed slides counterstained with Cresyl immunoreactivity per infused region. The resulting outlines were then copied to a transparency paper, individually matched to the corresponding baseline MR images and manually drawn with the Osirix ROI tool. Note that, in one instance (NHP1260) that, although near real-time MR imaging showed good distribution in the right thalamus, no transgene expression was detected. Therefore, we have excluded this case from the histology aspect of this study. It is not clear why this thalamic infusion did not transduce any neurons, but we suspect it might be due to vector aggregation during the procedure [25].

Percentage of HA Positive Neuronal Transduction

In adjacent sections (serially cut at 40 um thickness) immunostained against neuronal marker (anti-NeuN) or HA tag (anti-HA), randomized 20× magnification images (697.68×522.72 μm) were taken per targeted region (2 images per infusion site) across all NHP (N=4). In these images neuronal cell bodies stained against NeuN and HA were manually counted, their number tabulated and analyzed collectively per region infused (i.e. thalamus and brainstem). Comparison between NeuN and HA stained cell bodies was expressed as percentage of neurons positive for the HA tag per infused region.

Results—FIGS. 6-11

Near Real-Time MR Imaging of CED

Figure 6:
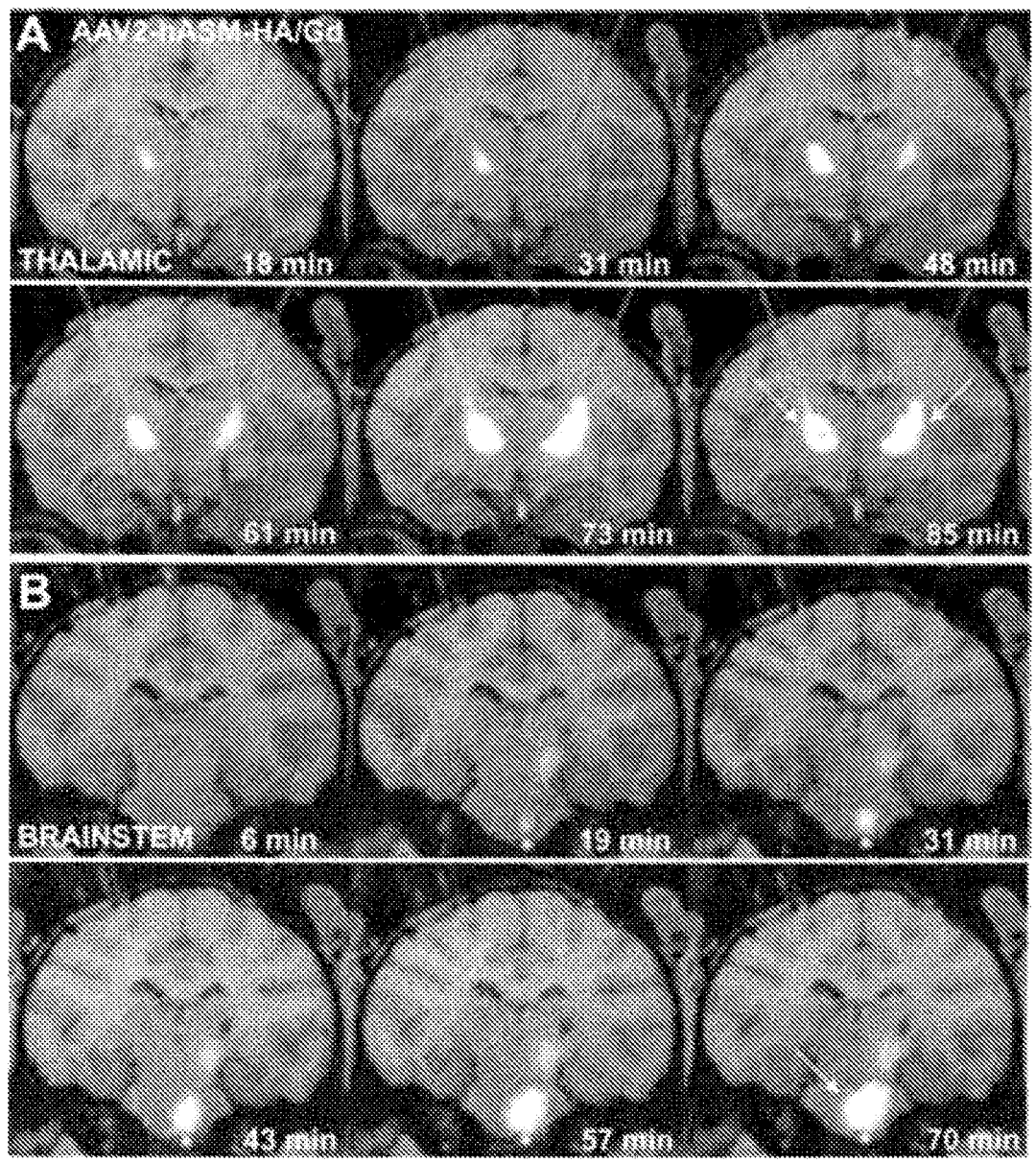
FIG. 6. Intra-Operative Use of Near Real-Time CED in the NHP Thalamus and Brainstem. Infusion of AAV2-hASM-HA/Gd visualized as a contrast demarcation on MRI indicate cannula tip placement in targeted region (A-B; white arrows). Note increase in infusate size as a function of time as demonstrated in sequential MR image acquisitions.

The outcome of intra-operative MRI imaging of cannula placement and monitoring of CED is illustrated in FIG. 6, where the placement of the cannula tip into pre-determined thalamic or brainstem structures and monitoring of the surrogate MR tracer was observed in all cases (FIG. 6A-B). These infusions were performed simultaneously and bilaterally in the thalamus followed by a single infusion in the brain stem (FIG. 6A-B, white arrows). We found radial convection of delivered infusate with no signs of leakage.

Volume Infused versus Volume of Distribution

Figure 7:
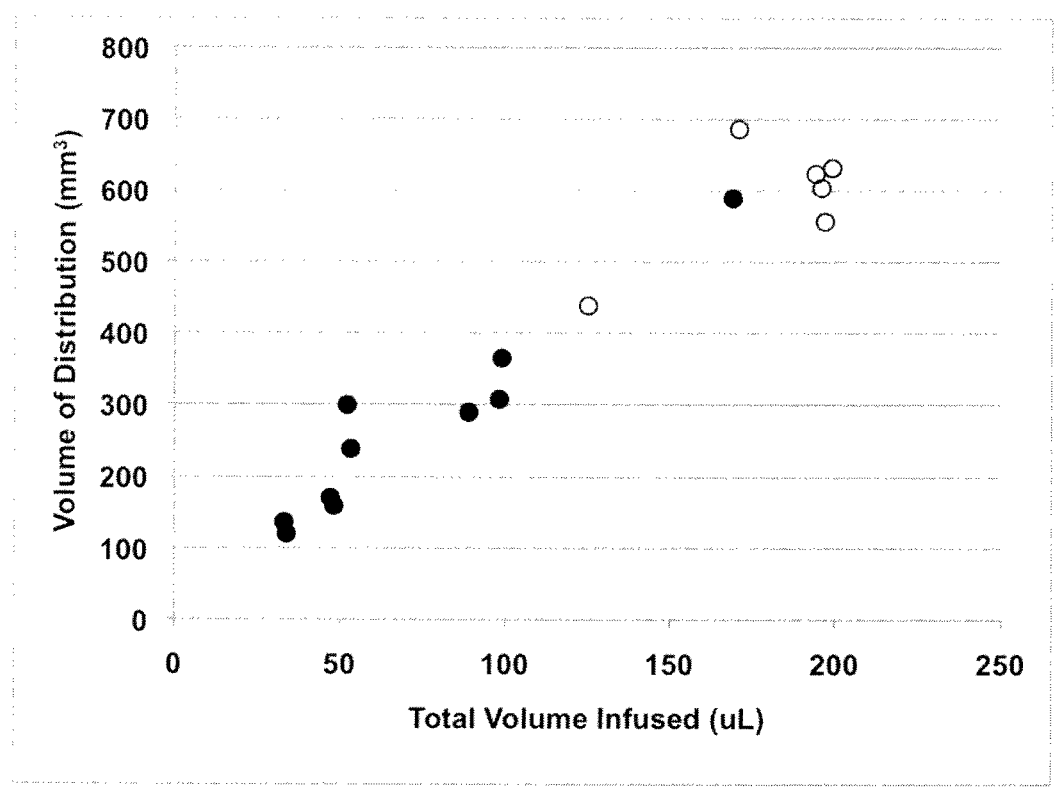
FIG. 7. Co-Infusion of AAV2-hASM-HA and Gd in thalamus (black symbol) and brainstem (white symbol). Single delivery of varying amounts of infusate into to the thalamus (black circles, N=10; Mean Vi:Vd ratio 3.86 [SEM+/−0.25]) and brainstem (white circles, N=6; Mean Vi:Vd ratio 3.3 [SEM+/−0.17]). Linear relationship between Vi to Vd (overall, N=16, $R^2$=0.93) with higher Vi delivered to the brainstem region as compared to the thalamus. No significant difference was found between ratios in these two regions (P>0.05).
Figure 8:
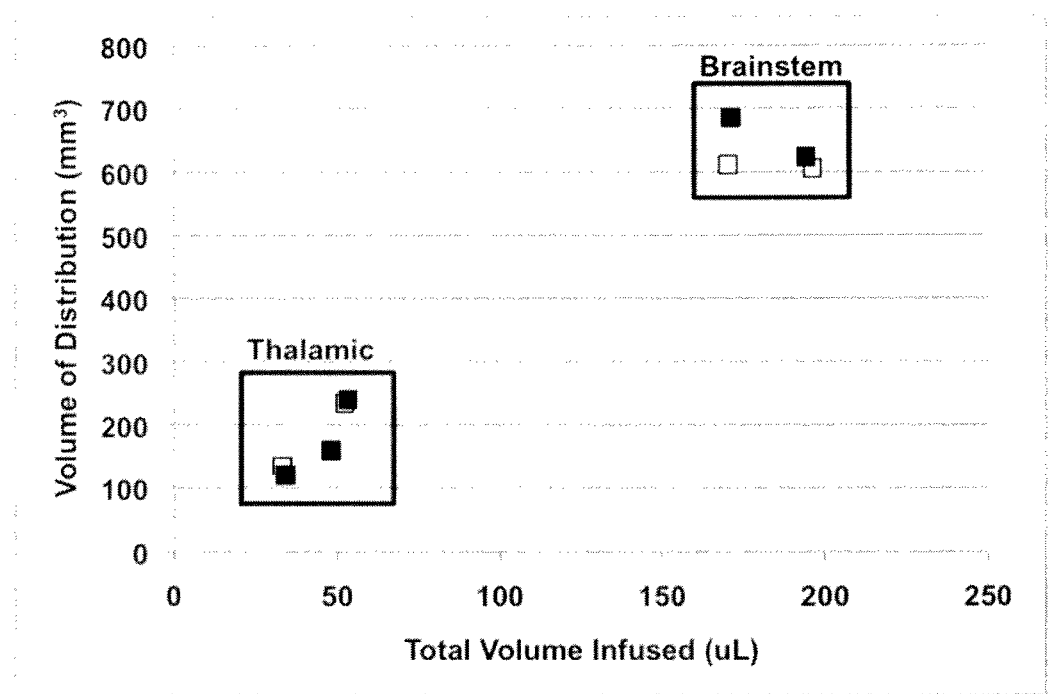
FIG. 8. Vi to Vd Comparison of Repeated Thalamic and Brainstem Infusions. Initial Vi:Vd delivery parameters during Gd only infusions (black boxes, N=5; Mean Vi:Vd ratio 3.74 [SEM+/−0.25], $R^2$=0.96) were replicated in later infusion consisting of AAV2-hASM-HA/Gd (white boxes, N=5; Mean Vi:Vd ratio 3.72 [SEM+/−0.24], $R^2$=0.98). Note consistent distribution patterns were observed in consecutive infusions with or without therapeutic agent (overall, N=10, $R^2$=0.96). No significant difference was found between primary or secondary infusions (P>0.05).

A direct linear relationship was found between Vi and Vd for both the thalamus and brainstem infusions ($R^2$=0.93; FIG. 7). The mean Vi to Vd ratio for all infusions (total of 16) as illustrated per region were: thalamus (N=10) was 3.86±0.25 SEM, and the ratio for the brainstem (N=6) was 3.3±0.17 SEM, which were not significantly different (p=0.14). More importantly, we demonstrated that repeated infusions of the MRI tracer into the same anatomical regions resulted in consistent infusate distribution (FIG. 8). We observed similar distribution patterns and Vi to Vd ratios in both thalamic and brainstem infusions with no statistical significance found between primary or secondary deliveries (p=0.96). Note that due to the size and volumetric capacity of the brainstem relative to thalamus, greater volumes were infused into the brainstem region with no apparent adverse neurological side effects.

Comparison of HA Tag and hASM Expression

Figure 9:
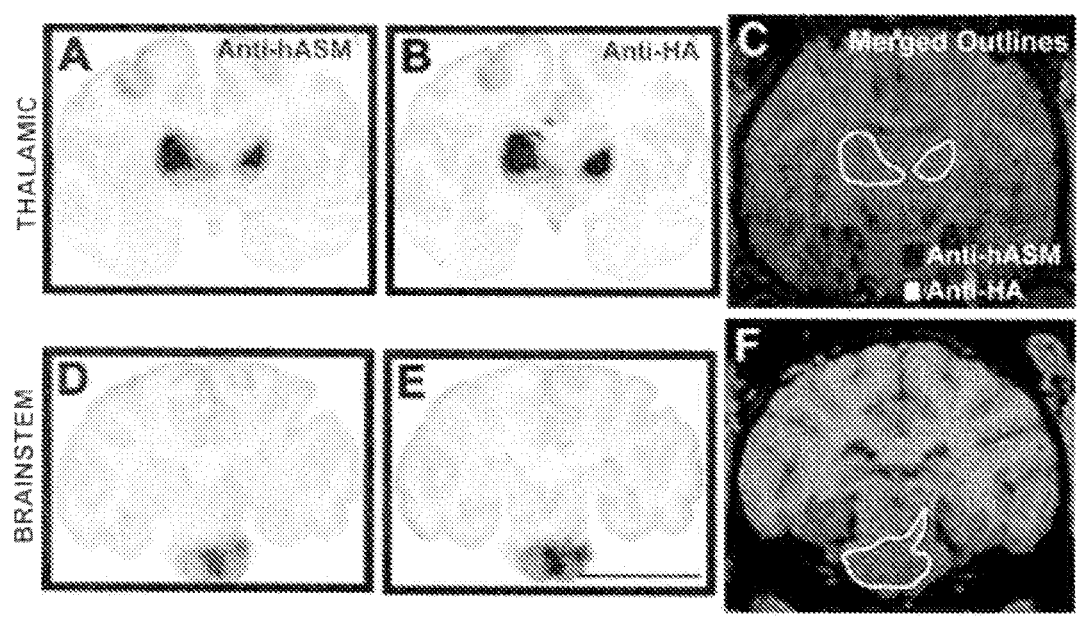
FIG. 9. Co-localization of hASM and HA staining in thalamus and brainstem. Similar immunoreactive regions stained for hASM or HA epitope in thalamic (A-C; left side, hASM [0.652 $cm^2$] and HA [0.616 $cm^2$]; right side, hASM [0.303 $cm^2$] and HA [0.277 $cm^2$]) and brainstem infused regions (D-F; hASM [0.817 $cm^2$] and HA [0.790 $cm^2$]). Note overlap of black and white lines representing area measured for each infusion (black line=anti-hASM; white line=anti-HA).

We anticipated that an HA epitope tag might be required in order to distinguish expressed hASM from endogenous NHP ASM. However, we found to our surprise that anti-HA and anti-hASM staining were superimposable with no evident staining of endogenous ASM (FIG. 9). This result indicates that AAV2-hASM-HA can easily drive expression of ASM to supra-physiologic levels that can be easily detected by immunostaining without the need for the HA tag. This comparison outlines transferred on to MR images (FIG. 9C, F), indicate transduction areas for each immunostain.

AAV Transduction and Distribution

Figure 10:
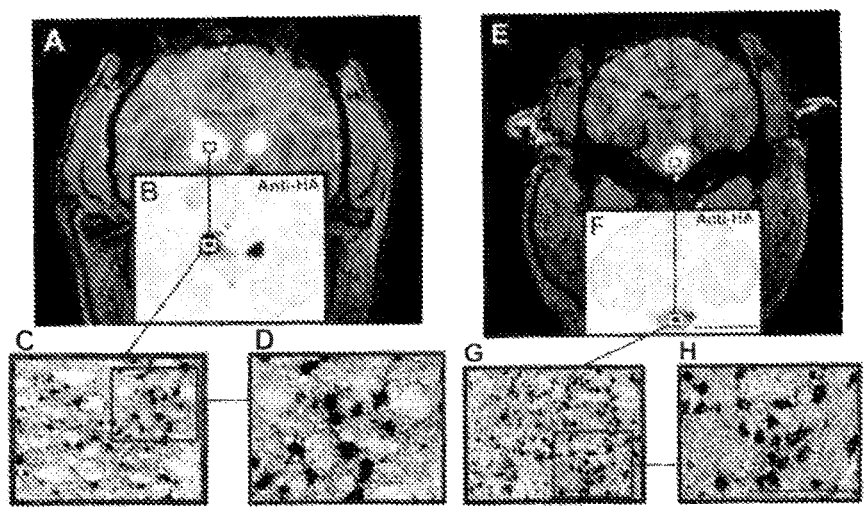
FIG. 10. AAV infusion and transduction in Thalamus and Brainstem. DICOM MR image representative of thalamic and brainstem infusion (A and E), as well as immunostained brain sections anatomically matched to corresponding MRI (B and F). High power magnification images demonstrate infusion epicenter containing significant neuronal transduction (HA expression) in each targeted region (C-D and G-H).
Figure 11:
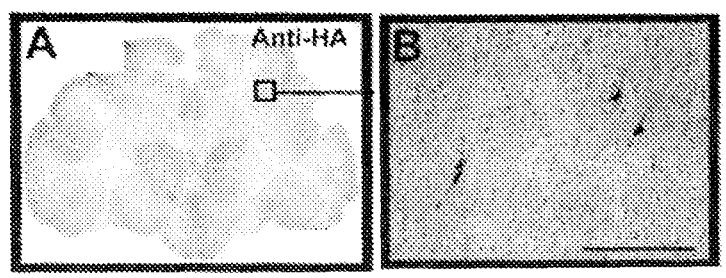
FIG. 11. Cortical expression of hASM-HA. (A) Direct infusate delivery into the thalamus revealed extensive distribution of therapeutic agent into the pre-frontal cortex region. (B) Higher magnification image indicate AAV transduction of cortical neurons (HA-positive).

Very high levels of transduction were achieved in the thalamus and brainstem after targeted infusions into these regions, as demonstrated in high-magnification images (FIG. 10). These images demonstrate transduction of cellular profiles resembling neurons or neuron-like morphology. CED delivery into the thalamus resulted in directed transduction and global distribution of this transgene to cortical regions not directly targeted by the infusion (FIG. 11, Table 2). This was evident by the detection of HA-positive cells dispersed throughout many cortical regions.

Efficiency of Transgene Expression

Another important factor in determining a successful infusion is the predictability between the distribution of MRI tracer and the resulting area of transgene expression. Tables 3, 4). Neuronal counting of immunostained cell bodies immunostained against neuronal marker (anti-NeuN) or HA epitope tag (anti-HA) revealed that in the thalamus up to 68% of neurons were positive for HA (SEM±11.3%) and in the brainstem 82% of neurons were positive (SEM±7.8%). Similarly, comparison between the area of Gd distribution and area of transgene expression and area of Gd distribution for thalamic infusions revealed 82% (SEM±8.4%) overlap, whereas for brainstem infusions we found that the expression area slightly exceeded the area of MR tracer distribution 117% (SEM±7.2%). Closer examination of transduced regions indicated that the vector specifically transduced neurons with no cellular transduction detected in astrocytes or microglia (data not shown). The finding that transduction was mainly observed in neurons is not surprising due to the AAV2 tropism for neurons. A modest increase in microglial activation is apparent in directly infused regions, however, this cellular activation was confined to the immediate convected area with no significant immune activation detected in cortical regions of treated NHP (data not shown).

TABLE 2

Transgene Expression/Distribution in the Cerebral Cortex

| Region | Area | NHP843 | | NHP1210 | | NHP1260 | | NHP1228 | |
|---|---|---|---|---|---|---|---|---|---|
| | | L | R | L | R | L | R | L | R |
| Pre-Frontal Cortex | 9/10/46 | xx | xxx | x | xx | xx | x | x | — |
| Broca's Area | 44/45 | x | x | x | xx | x | x | xx | x |
| Frontal Eye Field | 8 | xxx | xxx | x | xxx | xxx | xx | xxx | x |
| Secondary Motor Cortex | 6 | xx | xx | xx | xx | xxx | xx | xxx | xx |
| Anterior Cingulate Cortex | 24/32 | x | xx | — | x | x | x | xx | x |
| Somatosensory Cortex | 1/2/03 | xxx | xx | xx | xxx | xxx | x | xxx | x |
| Primary Motor Cortex | 4 | xx | xx | xx | xxx | xx | xx | xxx | xx |
| Posterior Cingulate Cortex | 23/31 | — | — | — | x | x | x | xx | x |

Distribution of transduction:
xxx - more than 50 positive cells;
xx - between 10-49 positive cells;
x - less than 9 positive cells.

TABLE 3

Distribution Area (Gd) and Transgene Expression in the Thalamus

| NHP (L/R Side) | Gd (cm$^2$) | Histology (cm$^2$) | Percentage (%) |
|---|---|---|---|
| 843 (L) | 0.82 | 0.88 | 107 |
| 1210 (L) | 0.21 | 0.20 | 94 |
| 1260 (L) | 0.39 | 0.28 | 71 |
| 1228 (L) | 0.41 | 0.19 | 45 |
| 843 (R) | 0.36 | 0.36 | 100 |
| 1210 (R) | 0.25 | 0.23 | 92 |
| 1228 (R) | 0.54 | 0.36 | 66 |
| | | Mean | 82% (SEM +/− 8.4) |

TABLE 4

Distribution Area (Gd) and Transgene Expression in the Brainstem

| NHP | Gd (cm$^2$) | Histology (cm$^2$) | Percentage (%) |
|---|---|---|---|
| 843 | 0.81 | 0.93 | 115 |
| 1210 | 0.65 | 0.88 | 135 |
| 1260 | 0.98 | 0.98 | 100 |
| 1228 | 0.79 | 0.92 | 116 |
| | | Mean | 117% (SEM +/− 7.2) |

AAV2-AADC Infusion

Three rhesus primates were infused with AAV2-AADC ($1 \times 10^{12}$ vg/ml) to the thalamus using methods described above. AAV2-AADC encodes the intracellular molecule aromatic L-amino acid decarboxylase (AADC). AADC staining was observed in distinct cortical regions, far from the needle tract, after thalamic AAV2-AADC infusion. (data not shown)

REFERENCES—FIGS. 5-11

1. Meikle, P J, et al. (1999). Prevalence of lysosomal storage disorders. *JAMA* 281: 249-254.
2. Pinto, I R, et al. (2004). Prevalence of lysosomal storage diseases in Portugal. *Eur J Hum Genet.* 12: 87-92.
3. Smith, E L, and Schuchman, E H (2008). The unexpected role of acid sphingomyelinase in cell death and the pathophysiology of common diseases. *FASEB J* 22: 3419-3431.
4. Barton, N W, et al. (1991). Replacement therapy for inherited enzyme deficiency—macrophage-targeted glucocerebrosidase for Gaucher's disease. *N Engl J Med* 324: 1464-1470.
5. Otterbach, B, and Stoffel, W (1995). Acid sphingomyelinase-deficient mice mimic the neurovisceral form of human lysosomal storage disease (Niemann-Pick disease). *Cell* 81: 1053-1061.
6. Berger, A, et al. (1995). Sphingosylphosphocholine, a signaling molecule which accumulates in Niemann-Pick disease type A, stimulates DNA-binding activity of the transcription activator protein AP-1. *Proc Natl Acad Sci USA* 92: 5885-5889.
7. He, X, et al. (1999). Characterization of human acid sphingomyelinase purified from the media of overexpressing Chinese hamster ovary cells. *Biochim Biophys Acta* 1432: 251-264.
8. Miranda, S R, et al. (2000). Infusion of recombinant human acid sphingomyelinase into niemann-pick disease mice leads to visceral, but not neurological, correction of the pathophysiology. *FASEB J* 14: 1988-1995.
9. Kitagawa, T (1987). An animal model of human acid sphingomyelinase deficiency (Niemann-Pick disease) and the study of its enzyme replacement (the Japan Society of Human Genetics award lecture). *Jinrui Idengaku Zasshi* 32: 55-69.
10. Peltola, M, et al. (1998). Adenovirus-mediated gene transfer results in decreased lysosomal storage in brain and total correction in liver of aspartylglucosaminuria (AGU) mouse. *Gene Ther* 5: 1314-1321.
11. Ziegler, R J, et al. (1999). Correction of enzymatic and lysosomal storage defects in Fabry mice by adenovirus-mediated gene transfer. *Hum Gene Ther* 10: 1667-1682.
12. Bosch, A, et al. (2000). Reversal of pathology in the entire brain of mucopolysaccharidosis type VII mice after lentivirus-mediated gene transfer. Hum Gene Ther 11: 1139-1150.
13. Kim, E Y, et al. (2004). Expression and secretion of human glucocerebrosidase mediated by recombinant lentivirus vectors in vitro and in vivo: implications for gene therapy of Gaucher disease. *Biochem Biophys Res Commun* 318: 381-390.
14. Barranger, J M, and Novelli, EA (2001). Gene therapy for lysosomal storage disorders. *Expert Opin Biol Ther* 1: 857-867.
15. Hsich, G, et al. (2002). Critical issues in gene therapy for neurologic disease. *Hum Gene Ther* 13: 579-604.
16. Watson, D J, and Wolfe, J H (2003). Lentiviral vectors for gene transfer to the central nervous system. Applications in lysosomal storage disease animal models. *Methods Mol Med* 76: 383-403.

17. Passini, M A, et al. (2005). AAV vector-mediated correction of brain pathology in a mouse model of Niemann-Pick A disease. *Mol Ther* 11: 754-762.
18. Kells, A P, et al. (2009). Efficient gene therapy-based method for the delivery of therapeutics to primate cortex. *Proc Natl Acad Sci USA* 106: 2407-2411.
19. Krauze, M T, et al. (2005). Real-time visualization and characterization of liposomal delivery into the monkey brain by magnetic resonance imaging. *Brain Res Brain Res Protoc* 16: 20-26.
20. Fiandaca, M S, et al. (2009). Real-time MR imaging of adeno-associated viral vector delivery to the primate brain. *Neuroimage* 47 Suppl 2: T27-35.
21. Yin, D., et al. (2009). Optimal Region of the Putamen for Image-Guided Convection-Enhanced Delivery of Therapeutics in Human and Non-human Primates. *Neuroimage* In Press.
22. Varenika, V, et al. (2008). Real-Time Imaging of CED in the Brain Permits Detection of Infusate Leakage *J Neurosurg* 109: 874-880.
23. Matsushita, T, et al. (1998). Adeno-associated virus vectors can be efficiently produced without helper virus. *Gene Ther* 5: 938-945.
24. Fiandaca, M S, et al. (2008). Image-guided convection-enhanced delivery platform in the treatment of neurological diseases. *Neurotherapeutics* 5: 123-127.
25. Wright, J F, et al. (2003). Recombinant adeno-associated virus: formulation challenges and strategies for a gene therapy vector. *Curr Opin Drug Discov Devel* 6: 174-178.
26. Lonser, R R, et al. (2007). Real-time image-guided direct convective perfusion of intrinsic brainstem lesions. Technical note. *J Neurosurg* 107: 190-197.
27. Janson, C, et al. (2002). Clinical protocol. Gene therapy of Canavan disease: AAV-2 vector for neurosurgical delivery of aspartoacylase gene (ASPA) to the human brain. *Hum Gene Ther* 13: 1391-1412.
28. Crystal, R G, et al. (2004). Clinical protocol. Administration of a replication-deficient adeno-associated virus gene transfer vector expressing the human CLN2 cDNA to the brain of children with late infantile neuronal ceroid lipofuscinosis. *Hum Gene Ther* 15: 1131-1154.
29. Krauze, M T, et al. (2008). Safety of real-time convection-enhanced delivery of liposomes to primate brain: A long-term retrospective. *Exp Neurol* 210: 638-644.
30. Sandberg, D I, et al. (2002). Effect of hyperosmolar mannitol on convection-enhanced delivery into the rat brain stem. *J Neurooncol* 58: 187-192.
31. Chen, M Y, et al. (1999). Variables affecting convection-enhanced delivery to the striatum: a systematic examination of rate of infusion, cannula size, infusate concentration, and tissue-cannula sealing time. *J Neurosurg* 90: 315-320.
32. Szerlip, N J, et al. (2007). Real-time imaging of convection-enhanced delivery of viruses and virus-sized particles. *J Neurosurg* 107: 560-567.
33. Rivera, V M, et al. (2005). Long-term pharmacologically regulated expression of erythropoietin in primates following AAV-mediated gene transfer. *Blood* 105: 1424-1430.
34. Eberling, J L, et al. (2008). Results from a phase I safety trial of hAADC gene therapy for Parkinson disease. *Neurology* 70: 1980-1983.
35. Christine, C W, et al. (2009). Safety and tolerability of putaminal AADC gene therapy for Parkinson's disease. *Neurology* In Press.
36. Marks, W J, Jr., et al. (2008). Safety and tolerability of intraputaminal delivery of CERE-120 (adeno-associated virus serotype 2-neurturin) to patients with idiopathic Parkinson's disease: an open-label, phase I trial. *Lancet Neurol* 7: 400-408.
37. Kaplitt, M G, et al. (2007). Safety and tolerability of gene therapy with an adeno-associated virus (AAV) borne GAD gene for Parkinson's disease: an open label, phase I trial. *Lancet* 369: 2097-2105.
38. Bartlett, J S, et al., (1998). Selective and rapid uptake of adeno-associated virus type 2 in brain. *Hum Gene Ther* 9: 1181-1186.
39. Daadi, M M, et al. (2006). Distribution of AAV2-hAADC-transduced cells after 3 years in Parkinsonian monkeys. *Neuroreport* 17: 201-204.
40. Bankiewicz, K S, et al. (2006). Long-Term Clinical Improvement in MPTP-Lesioned Primates after Gene Therapy with AAV-hAADC. *Mol Ther* 14: 564-570.
41. Barbon, C M, et al. (2005). AAV8-mediated hepatic expression of acid sphingomyelinase corrects the metabolic defect in the visceral organs of a mouse model of Niemann-Pick disease. *Mol Ther* 12: 431-440.
42. Dodge, J C, et al. (2005). Gene transfer of human acid sphingomyelinase corrects neuropathology and motor deficits in a mouse model of Niemann-Pick type A disease. *Proc Natl Acad Sci USA* 102: 17822-17827.
43. Passini, M A, et al. (2007). Combination brain and systemic injections of AAV provide maximal functional and survival benefits in the Niemann-Pick mouse. *Proc Natl Acad Sci USA* 104: 9505-9510.
44. Cearley, C N, and Wolfe, J H (2007). A single injection of an adeno-associated virus vector into nuclei with divergent connections results in widespread vector distribution in the brain and global correction of a neurogenetic disease. *J Neurosci* 27: 9928-9940.
45. Marathe, S, et al. (2000). Creation of a mouse model for non-neurological (type B) Niemann-Pick disease by stable, low level expression of lysosomal sphingomyelinase in the absence of secretory sphingomyelinase: relationship between brain intra-lysosomal enzyme activity ad central nervous system function. *Hum Gene Ther* 9: 1967-1976.
46. Burger, C, et al., (2004). Recombinant AAV viral vectors pseudotyped with viral capsids from serotypes 1, 2 and 5 display differential efficiency and cell tropism after delivery to different regions of the central nervous system. *Mol Ther* 10: 302-317.
47. Gagliardi, C, and Bunnell, BA (2009). Large animal models of neurological disorders for gene therapy. *ILAR J* 50: 128-143.

All citations are expressly incorporated herein in their entirety by reference.

We claim:

1. A method for delivering an Adeno Associated Virus (AAV) therapeutic agent to neurons of the cerebral cortex in a primate by anterograde transport from the thalamus, comprising administering said AAV therapeutic agent into the thalamus of said primate by convection enhanced delivery (CED) at an infusion rate greater than 0.5 µl/min, thereby delivering the AAV therapeutic agent to neurons of multiple cortical layers of the primate cerebral cortex.

2. The method according to claim 1, wherein said AAV therapeutic agent is administered to more than one location in the thalamus.

3. The method according to claim 2, wherein more than one cannula is used to administer said AAV therapeutic agent.

4. The method according to claim 1, comprising repeated administration of said AAV therapeutic agent.

5. The method according to claim 1, wherein said AAV therapeutic agent is delivered to more than one functional area of the cerebral cortex.

6. The method according to claim 1, wherein said AAV therapeutic agent is delivered to more than one lobe of the cerebral cortex.

7. The method according to claim 1, wherein said AAV therapeutic agent is an AAV particle comprising a nucleic acid encoding a therapeutic protein.

8. The method according to claim 1, wherein said method comprises delivering the AAV therapeutic agent to cortical layers II, III, and/or IV.

9. The method according to claim 1, wherein said AAV is selected from the group consisting of AAV2, AAV3, AAV4, AAV5, AAV7, AAV8, and AAV9.

10. The method according to claim 1, wherein the CED comprises an infusion rate greater than 0.7 µl/min.

11. The method according to claim 1, wherein the method comprises delivering the AAV therapeutic agent to neurons of more than one lobe of the cerebral cortex.

12. The method according to claim 1, wherein the method comprises delivering the AAV therapeutic agent to neurons of Cortical Areas 9 and 10 and to neurons of any one of Cortical Area 6; Cortical Areas 3, 1, or 2; or Cortical Area 4.

13. The method according to claim 1, wherein the method comprises delivering the AAV therapeutic agent to neurons of Cortical Areas 1, 2, 3, 4, 6, 8, 9, and 10.

* * * * *